(12) United States Patent
Ramamurthy

(10) Patent No.: US 7,943,038 B2
(45) Date of Patent: May 17, 2011

(54) METHOD FOR PRODUCING OLEFINS USING A DOPED CATALYST

(75) Inventor: Pritham Ramamurthy, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 545 days.

(21) Appl. No.: 12/021,364

(22) Filed: Jan. 29, 2008

(65) Prior Publication Data

US 2009/0192343 A1    Jul. 30, 2009

(51) Int. Cl.
*C10G 11/05* (2006.01)

(52) U.S. Cl. ........ 208/119; 208/106; 208/113; 208/118; 208/120.01; 208/120.25; 208/120.35; 585/648; 585/650; 585/651; 585/653

(58) Field of Classification Search .................. 585/648, 585/650, 651, 653; 208/106, 113, 121, 122, 208/118, 119, 120.01, 120.25, 120.35
See application file for complete search history.

(56) References Cited

U.S. PATENT DOCUMENTS

| | | | | |
|---|---|---|---|---|
| 3,894,934 | A | * | 7/1975 | Owen et al. ................. 208/78 |
| 4,088,568 | A | * | 5/1978 | Schwartz .................... 208/121 |
| 4,091,046 | A | | 5/1978 | Dixon |
| 4,329,516 | A | | 5/1982 | Al-Muddarris |
| 4,415,440 | A | * | 11/1983 | Roberts et al. ............. 208/120.2 |
| 4,513,162 | A | | 4/1985 | Al-Muddarris |
| 4,754,078 | A | | 6/1988 | Vora et al. |
| 4,766,266 | A | | 8/1988 | Khoobiar |
| 4,806,695 | A | | 2/1989 | Vora et al. |
| 4,816,607 | A | | 3/1989 | Vora et al. |
| 4,835,127 | A | | 5/1989 | Eastman et al. |
| 4,868,342 | A | | 9/1989 | Verson |
| 4,997,545 | A | | 3/1991 | Krishna et al. |
| 5,008,467 | A | | 4/1991 | Vora et al. |
| 5,043,522 | A | | 8/1991 | Leyshon et al. |
| 5,105,024 | A | | 4/1992 | McKay et al. |
| 5,113,023 | A | | 5/1992 | Anderson |
| 5,166,455 | A | | 11/1992 | Chin et al. |
| 5,198,590 | A | | 3/1993 | Sofranko et al. |
| 5,447,622 | A | * | 9/1995 | Kerby et al. ................. 208/78 |
| 5,523,502 | A | | 6/1996 | Rubin |
| 5,981,818 | A | * | 11/1999 | Purvis et al. ................. 585/519 |
| 6,069,287 | A | | 5/2000 | Ladwig et al. |
| 6,287,522 | B1 | | 9/2001 | Lomas |

(Continued)

OTHER PUBLICATIONS

"UOP Fluid Catalytic Cracking (FCC) and Related Processes," Process Technology and Equipment, 2003, pp. 1-4, UOP LLC, Des Plaines, IL.

*Primary Examiner* — Glenn A Caldarola
*Assistant Examiner* — Bradley Etherton
(74) *Attorney, Agent, or Firm* — KBR IP Legal Dept.

(57) ABSTRACT

Processes for producing one or more olefins are provided. In one or more embodiments, a doped catalyst can be prepared by fluidizing one or more coked-catalyst particles in the presence of one or more oxidants to provide a fluidized mixture. At least a portion of the coke can be removed from the coked-catalyst particles to provide regenerated catalyst particles. One or more doping agents can be distributed throughout the fluidized mixture, depositing on the surface of the regenerated catalyst particles to provide doped catalyst particles. One or more hydrocarbon feeds can be fluidized with the doped catalyst particles to provide a reaction mixture which can be cracked to provide a first product containing propylene, ethylene, and butane.

28 Claims, 6 Drawing Sheets

U.S. PATENT DOCUMENTS

| | | |
|---|---|---|
| 6,339,181 B1 | 1/2002 | Chen et al. |
| 6,538,169 B1 * | 3/2003 | Pittman et al. ............ 585/653 |
| 6,936,239 B2 | 8/2005 | Rao |
| 6,964,934 B2 | 11/2005 | Brady et al. |
| 6,969,692 B2 | 11/2005 | Brady et al. |
| 6,977,321 B1 | 12/2005 | Dath et al. |
| 7,033,487 B2 | 4/2006 | O'Connor et al. |
| 7,034,195 B2 | 4/2006 | Schindler et al. |
| 7,128,827 B2 * | 10/2006 | Tallman et al. ............ 208/78 |
| 7,135,602 B1 | 11/2006 | Le Van Mao |
| 2002/0087040 A1 | 7/2002 | Marchionna et al. |
| 2006/0004242 A1 * | 1/2006 | Verma et al. ............ 585/809 |

* cited by examiner

METHOD FOR PRODUCING OLEFINS USING A DOPED CATALYST

BACKGROUND

1. Field

The present embodiments generally relate to systems and methods for adjusting the activity or selectivity of a catalyst for olefin production. More particularly, embodiments of the present invention relate to systems and methods for selectively adjusting the activity or selectivity of a catalyst for hydrocarbon processing through an in-situ addition of one or more doping agents during regeneration of the catalyst and olefins produced therefrom.

2. Description of the Related Art

Hydrocarbon cracking is a method where under controlled temperature, pressure, and reaction conditions, one or more carbon-carbon bonds in a heavy molecular weight hydrocarbon can be broken (or "cracked") to form two or more lower molecular weight hydrocarbons or rearranged, with or without hydrogen transfer, to different molecules, including olefinic and aromatic compounds. Generally temperature, pressure and residence time within the cracker are adjusted to favor the production of desirable compounds. In fluidized catalytic crackers ("FCC"), a catalyst is employed to increase the yield of preferred lower molecular weight hydrocarbons, and to compensate for variations in hydrocarbon feedstock composition. Various additives or doping agents can be added to the catalyst to provide a doped catalyst where high performance or highly selective catalysts are desired.

Traditional production of doped FCC catalysts involves a multi-step process where the catalyst and the doping agent are uniformly dispersed within a solution. Heat is often applied to the solution to precipitate the catalyst. While a uniform, highly porous catalyst can thus be produced, the doping agent is dispersed more-or-less uniformly throughout the catalyst particle. Alternatively, the solid catalyst is dispersed in a solution containing the doping agent and dried. Since cracking occurs only on the exposed surfaces of the catalyst particle (hence the desirability of a highly porous catalyst), doping agent embedded deep within the catalyst matrix is unavailable to the cracking process. Where the supply of doping agent is limited, or where the doping agents are expensive or environmentally sensitive, the quantity of doping agent "lost" within the catalyst matrix may limit the overall availability of catalyst, may dramatically increase the cost of fresh catalyst, or may dramatically increase the cost of disposal for spent catalyst.

Where the composition of an incoming hydrocarbon feedstock is highly variable, it may be desirable to adjust the doping agent type or concentration to maintain a consistent finished product. With a traditional catalyst, since the doping agent remains embedded within the catalyst matrix, changing catalysts and/or doping agents in response to feedstock variations often requires complete replacement of the catalyst charge in the system. Such replacements are inefficient and costly, particularly as the variability of hydrocarbon feedstocks increases due to the frequent sourcing from multiple production regions scattered across wide geographic areas.

Given increasing reliance on the cracking of marginal quality crude oil feedstocks having highly variable compositions, there is a need therefore, for a method and process for rapidly adjusting the quantity or composition of doping agents used in FCC catalysts.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Processes for producing one or more olefins are provided. In one or more embodiments, a doped catalyst can be prepared by fluidizing one or more coked-catalyst particles in the presence of one or more oxidants to provide a fluidized mixture. At least a portion of the coke can be removed from the coked-catalyst particles to provide regenerated catalyst particles. One or more doping agents can be distributed throughout the fluidized mixture, depositing on the surface of the regenerated catalyst particles to provide doped catalyst particles. One or more hydrocarbon feeds can be fluidized with the doped catalyst particles to provide a reaction mixture which can be cracked to provide a first product containing propylene, ethylene, and butane.

Figure 1:
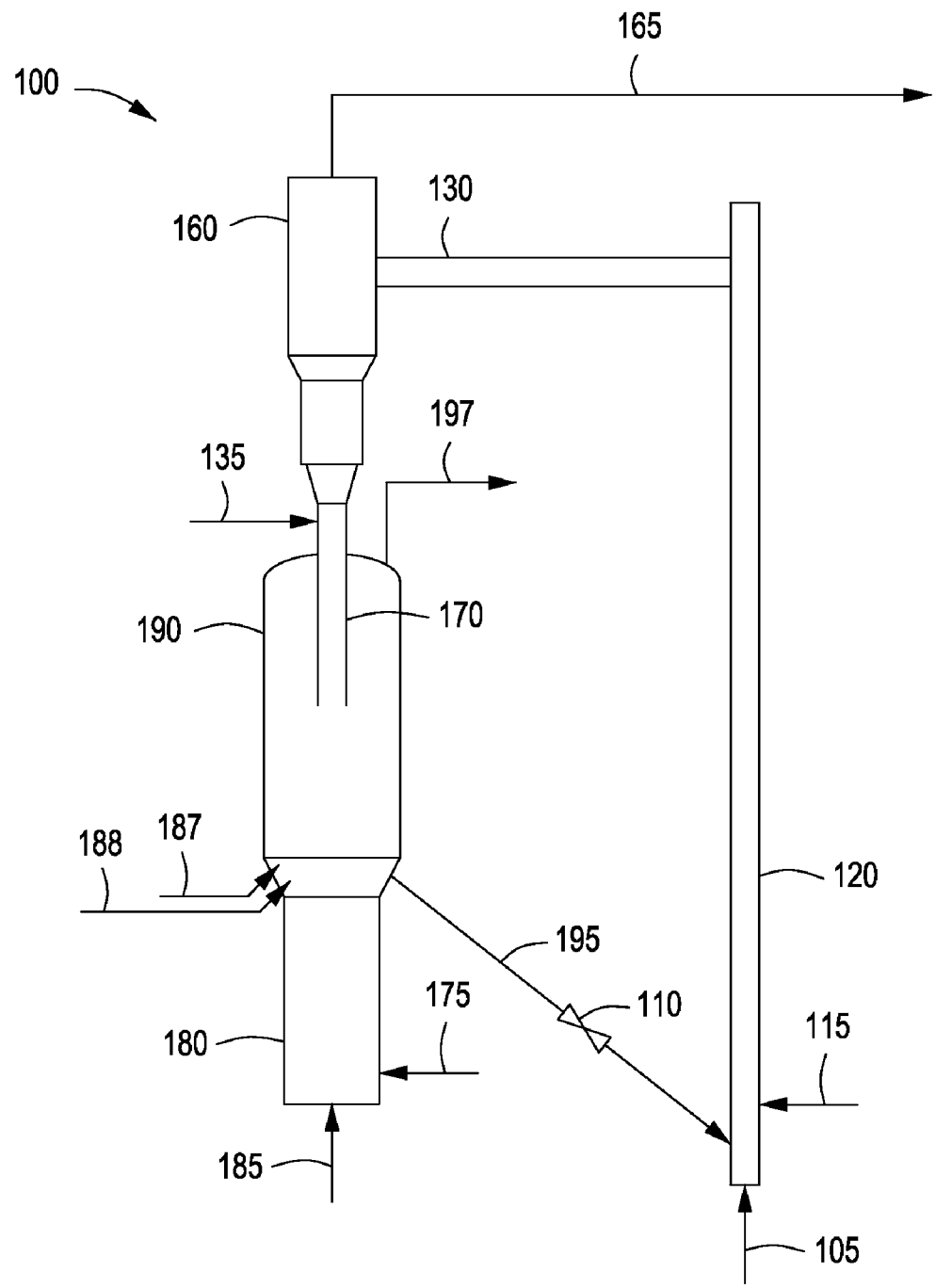
FIG. 1 depicts an illustrative system for regenerating and doping catalyst according to one or more embodiments described.

With reference to the figures, FIG. 1 depicts an illustrative system 100 for regenerating and doping catalyst, according to one or more embodiments. In one or more embodiments, the system 100 can be a fluidized catalytic cracker ("FCC") or other suitable system having one or more risers 120, ducts 130, separation zones 160, combustion zones 180, and regeneration zones 190. In one or more embodiments, steam via line 105, a hydrocarbon feed via line 115 and a doped catalyst via line 195 can be introduced to the one or more risers 120, forming a fluidized mixture ("reaction mixture") therein. The steam via line 105 and the doped catalyst via line 195 can be fed separately to the riser 120 as shown in FIG. 1, or the steam and the doped catalyst can be mixed and fed together as a mixture to the riser 120.

In one or more embodiments, heat in the riser 120 provided by the steam via line 105 and the doped catalyst via line 195 can vaporize the hydrocarbon feed via line 115 entering the riser 120, and forming a mixture ("reaction mixture") therein. In one or more embodiments, supplemental heat and/or firing can be provided to the one or more risers 120 using waste heat provided from the one or more combustion zones 180 and/or regeneration zones 190. Within the riser 120, the hydrocarbons within the reaction mixture can be substantially cracked into one or more hydrocarbons and hydrocarbon by-products to provide a first product mixture. In one or more embodiments, at least a portion of the hydrocarbon by-products present in the riser 120 can deposit on the surface of the catalyst particles, forming coked-catalyst particles. Thus, the first product mixture exiting the riser 120 can contain coked-catalyst particles suspended in gaseous hydrocarbons, hydrocarbon by-products, steam, and other inerts.

In one or more embodiments, the velocity of the reaction mixture flowing through the riser 120 can range from about 3 m/sec (10 ft/sec) to about 27 m/sec (90 ft/sec), about 6.1 m/sec (20 ft/sec) to about 24.4 m/sec (80 ft/sec), or about 9.1 m/sec (30 ft/sec) to about 21.3 m/sec (70 ft/sec). In one or more embodiments, the residence time of the reaction mixture in the riser 120 can be less than about 20 seconds, about 10 seconds, about 8 seconds, about 4 seconds, or about 2 seconds.

In one or more embodiments, the first product mixture can flow, via the duct 130, to the one or more separation zones 160 where the coked-catalyst particles can be separated from the gaseous hydrocarbons, steam, and inerts. The separation zone 160 can be a section of the system 100 having a larger cross-sectional area than either the riser 120 or the duct 130 to reduce the velocity of the gas, allowing the heavier coked-catalyst particles to separate from one or more gaseous hydrocarbons, steam, and inerts. In one or more embodiments, a steam purge can be added via line 135 to the separation zone 160 to assist in separating the gaseous hydrocarbons from the coked-catalyst particles, i.e. stripping the gaseous hydrocarbons from the solids.

In one or more embodiments, the gaseous hydrocarbons can be removed from the separation zone 160 via line 165. The gaseous hydrocarbons in line 165 can be further processed, such as by dehydrating or fractionating to provide one or more finished products including, but not limited to, one or more olefins, paraffins, aromatics, mixtures thereof, derivatives thereof, and/or combinations thereof. The solids, i.e. coked-catalyst particles, can free fall through the separation zone discharge 170 toward the combustion and regeneration zone 180, 190.

In one or more embodiments, within the combustion and regeneration zones 180, 190, the coked-catalyst particles can be combined with one or more oxidizing agents introduced via line 185 including, but not limited to air, oxygen, and/or oxygen enriched air. The one or more oxidizing agents can react with the carbonaceous matter on the coked-catalyst particles to combust or otherwise burn the carbon ("coke") off the surface of the catalyst particle. In one or more embodiments, fresh, unused, catalyst can be added via line 175 to the combustion zone 180, and/or regeneration zones 190 (not shown). The removal of the coke from the surface of the catalyst particle can re-expose the reactive surfaces of the catalyst, thereby "regenerating" the catalyst particle, permitting its reuse. Combustion by-products, such as carbon monoxide and carbon dioxide, can be removed from the system 100 as a waste gas via line 197.

In one or more embodiments, within the regeneration zone 190 a fluidized mixture, containing substantially de-coked (i.e. "clean") catalyst particles, carbon monoxide, carbon dioxide, and the one or more oxidizing agents can be combined with one or more doping agents introduced via line 187. The dispersal and deposition of the one or more doping agents on the regenerated catalyst can be enhanced by the high temperature and turbulence present in the regeneration zone 190. In one or more embodiments, the regeneration zone 190 can operate at a temperature range of from about 480° C. (900° F.) to about 900° C. (1,650° F.); from about 590° C. (1,100° F.) to about 815° C. (1,500° F.); or from about 650° C. (1,200° F.) to about 815° C. (1,500° F.).

In one or more embodiments, the one or more doping agents can be mixed with a supplemental fuel, for example natural gas, and introduced to the regeneration zone 190 via line 188. The use of supplemental fuel can provide additional heat within the regeneration zone 190, further enhancing the regeneration of the coked-catalyst particles therein.

In one or more embodiments, the turbulence within the regeneration zone 190 can assist the even dispersion of the one or more doping agents within the fluidized mixture, increasing the contact between the one or more doping agents with the reactive surfaces on the regenerated catalyst. In contrast, the one or more doping agents in a traditional, homogeneously doped, catalyst are dispersed within the catalyst particles. Consequently, less doping agent can be used to achieve the same concentration of doping agent on the surface of the regenerated catalyst particle. Also, changing doping agents in response to changing process conditions and/or hydrocarbon feed composition can be more readily achieved since little or no entrained doping agent exists within the catalyst particle, i.e. the interior matrix of the catalyst particle. For example, the doping agent can be changed simply by changing the type and/or composition of the doping agent added to the regeneration zone 180.

In one or more embodiments, the selection of an appropriate doping agent or additive or blend of two or more doping agents or additives can be based upon the composition of the incoming hydrocarbon feed via line 115, and/or desired gaseous hydrocarbons in the first product exiting the catalytic cracker via line 165. For example, the addition of a class 2 doping agent such as magnesium or barium can preferentially increase the production of ethylene in the first product in line 165. The addition of a class 13 doping agent such as gallium can result in the increased production of aromatic hydrocarbons in the first product in line 165. The addition of class 8, 9, or 10 doping agents such as ruthenium, rhodium or palladium can preferentially increase the production of propylene in the first product in line 165.

In one or more embodiments, doped catalyst particles, containing regenerated catalyst particles with one or more doping agents or additives can be returned to the one or more risers 120 via line 195. In one or more embodiments, the flow of regenerated catalyst from the regeneration zone 190 can be controlled using one or more valves 110, which can be manually or automatically adjusted or controlled based upon parameters derived from process temperatures, pressures, flows and/or other process conditions. In one or more embodiments, at least 90% wt, at least 95% wt, at least 99% wt, at least 99.99% wt, at least 99.9975% wt, or at least 99.999% wt of the total doped catalyst originally introduced to the riser 120 via line 195 can be regenerated, doped with one or more doping agents, and recycled back to the riser 120.

In one or more embodiments, the hydrocarbon feed in line 115 can include, but is not limited to, mixed olefins, paraffins, mixtures thereof, and/or any combination thereof. In one or more embodiments, the hydrocarbon feed can originate from a refinery. For example, the hydrocarbon feed can be a gas mixture resulting from the distillation of crude oil. In one or more embodiments, the hydrocarbon feed can contain hydrocarbon compounds containing 11 or fewer carbon atoms. In one or more embodiments, the hydrocarbon feed can include from about 0.1% vol to 5% vol methane; from about 0.1% vol to about 10% vol ethane; from about 0.1% vol to about 30% vol propane. In one or more embodiments, the hydrocarbon feed can contain from about 0% vol to about 35% vol butane; and from about 0% vol to about 20% vol pentane and heavier hydrocarbons. In one or more embodiments, the hydrocarbon feed can include at least 60% wt $C_2$-$C_{11}$ olefins and paraffin.

In one or more embodiments, the hydrocarbon feed introduced via line 115 can be pre-heated prior to introduction to the riser 120. Although not shown in FIG. 1, a regenerative heat exchanger using waste process heat can be used to pre-heat the hydrocarbon feed. In one or more embodiments, the temperature of the hydrocarbon feed can range from about 370° C. (700° F.) to about 790° C. (1,450° F.), about 425° C. (800° F.) to about 700° C. (1,300° F.), or about 480° C. (900° F.) to about 700° C. (1,300° F.). In one or more embodiments, the pressure of the hydrocarbon feed can range from about 100 kPa (0 psig) to about 3,450 kPa (485 psig), about 100 kPa (0 psig) to about 2,750 kPa (385 psig), or about 100 kPa (0 psig) to about 350 kPa (35 psig).

In one or more embodiments, the hydrocarbon feed introduced via line 115 can be partially or completely vaporized prior to introduction to the one or more risers 120. In one or more embodiments, the hydrocarbon feed can be at least about 10 vol % to about 100 vol %; about 20 vol % to about 60 vol %; about 30 vol % to about 60 vol %; about 40 vol % to about 60 vol %; or about 50 vol % to about 60 vol % vaporized. In one or more embodiments, the hydrocarbon feed can be at least about 70 vol % to about 100 vol %; about 80 vol % to about 100 vol %; or about 90 vol % to about 100 vol % vaporized. In one or more embodiments, the hydrocarbon feed can be a minimum of 80% wt vaporized; 85% wt vaporized; 90% wt vaporized; 95% wt vaporized; or about 99% wt vaporized prior to introduction to the riser 120. In one or more embodiments, within the riser 120, pressure and temperature can be adjusted either manually or automatically to compensate for variations in hydrocarbon feed composition and to maximize the yield of preferred hydrocarbons obtained by cracking the hydrocarbon feed in the presence of the one or more doped catalysts.

In one or more embodiments, the steam introduced via line 105 to the one or more risers 120 can be saturated. The pressure of the saturated steam can be a minimum of about 1,000 kPa (130 psig), about 2,000 kPa (275 psig), about 4,000 kPa (565 psig), or about 6,000 kPa (855 psig). In one or more embodiments, the pressure of the saturated steam can range from about 100 kPa (0 psig) to about 8,300 kPa (1,190 psig); about 100 kPa (0 psig) to about 4,000 kPa (565 psig); or about 100 kPa (0 psig) to about 2,000 kPa (275 psig).

In one or more embodiments, the steam introduced via line 105 to the one or more risers 120 can be superheated. In one or more embodiments, where superheated steam is used, the pressure of the superheated steam can be a minimum of about 1,000 kPa (130 psig), about 2,000 kPa (276 psig), about 4,000 kPa (565 psig), or about 6,000 kPa (855 psig). In one or more embodiments, the pressure of the superheated steam can range from about 100 kPa (0 psig) to about 8,300 kPa (1,190 psig); about 100 kPa (0 psig) to about 4,000 kPa (565 psig); or about 100 kPa (0 psig) to about 2,000 kPa (275 psig). In one or more embodiments, the temperature of the superheated steam can be a minimum of about 200° C. (400° F.), about 230° C. (450° F.), about 260° C. (500° F.), or about 290° C. (550° F.).

In one or more embodiments, the steam can be introduced via line 105 to the riser 120 at a rate proportionate to the hydrocarbon feed rate via line 115. In one or more embodiments, the steam-to-hydrocarbon feed weight ratio can range from about 1:20 to about 50:1; from about 1:20 to about 20:1; or from about 1:10 to about 20:1.

In one or more embodiments, the catalyst can include, but is not limited to one or more zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), or high activity zeolite catalysts. In one or more embodiments, the catalyst-to-oil weight ratio can range from about 5:1 to about 70:1; from about 8:1 to about 25:1; or from about 12:1 to about 18:1. In one or more embodiments, the temperature of the doped catalyst, prior to introduction to the riser 120, can range from about 200° C. (400° F.) to about 815° C. (1,500° F.); about 200° C. (400° F.) to about 760° C. (1,400° F.); or about 200° C. (400° F.) to about 675° C. (1,250° F.).

In one or more embodiments, the first product in line 165 can include from about 5% wt to about 30% wt $C_2$; about 5% wt to about 60% wt $C_3$; about 5% wt to about 40% wt $C_4$; about 5% wt to about 50% wt $C_5$ and heavier hydrocarbons. In one or more embodiments, the temperature of the first product in line 165 can range from about 425° C. (800° F.) to about 815° C. (1,500° F.); about 450° C. (850° F.) to about 760° C. (1,400° F.); or about 480° C. (900° F.) to about 730° C. (1,350° F.).

Figure 2:
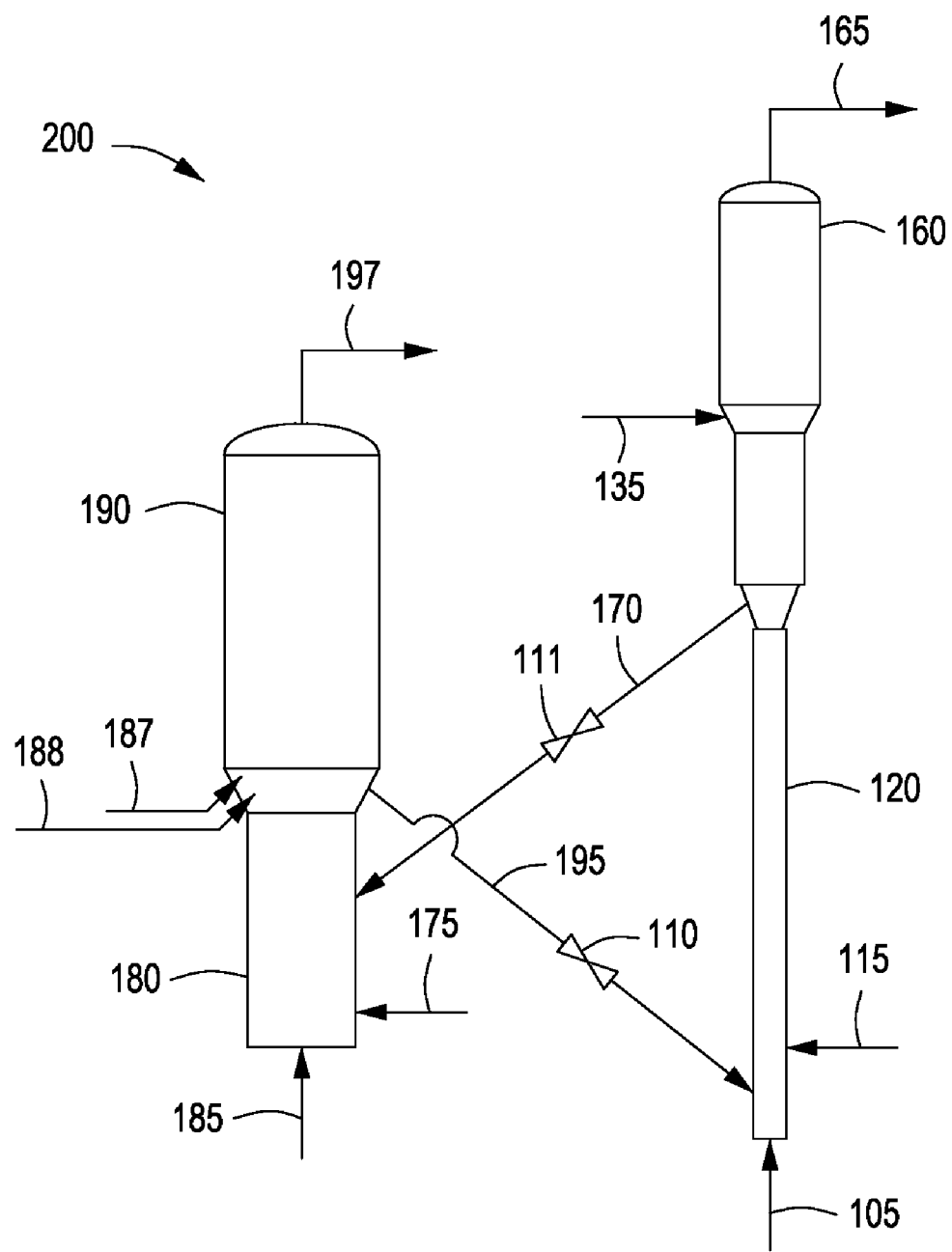
FIG. 2 depicts another illustrative system for regenerating and doping catalyst according to one or more embodiments described.

FIG. 2 depicts another illustrative system 200 for regenerating and doping catalyst according to one or more embodiments. In one or more embodiments, the system 200 can include one or more risers 120, separation zones 160, combustion zones 180, and regeneration zones 190. In one or more embodiments, the separation zone 160 can be disposed above the riser 120 as depicted in FIG. 2. In one or more embodiments, the separation zone 160 can include a separation zone discharge 170 which can provide fluid communication between the separation zone 160 and one or more combustion zones 180. The separation zone discharge 170 can include one or more valves 111 to manually or automatically adjust or control the flow of coked-catalyst particles to the combustion zone 180 based on parameters derived from process temperatures, pressures, flows, and/or other process conditions.

As described above, the hydrocarbon feed via line 115, steam via line 105 and the one or more doped catalysts via line 195 can be introduced to the riser 120, forming the reaction mixture therein. In one or more embodiments, at least a portion of the hydrocarbons present in the reaction mixture can crack or otherwise react to form one or more gaseous hydrocarbons and one or more hydrocarbon by-products. In the reaction mixture within the riser 120, at least a portion of the hydrocarbon by-products can deposit onto the doped catalyst particles, forming coked-catalyst particles. In one or more embodiments, the first product mixture exiting the riser 120 can contain coked-catalyst particles suspended in gaseous hydrocarbons, hydrocarbon by-products, steam, and other inerts.

In one or more embodiments, the first product mixture can be introduced to the separation zone 160 wherein the coked-catalyst particles can be separated from the gaseous hydrocarbons. The gaseous hydrocarbons can be removed via line 165 from the separation zone 160, while the separated coked-catalyst particles can fall through the separation zone 160, and into the separation zone discharge 170. In one or more embodiments, one or more valves 111 can be located within the separation zone discharge 170 to control the flow of separated coked-catalyst particles from the separation zone 160 to the combustion zone 180.

In one or more embodiments, fresh, unused, catalyst can be added via line 175 to the combustion zone 180, and/or regeneration zone 190 (not shown). In one or more embodiments, within the combustion zone 180 the coked-catalyst particles can be mixed with one or more oxidants, introduced via line 185, and combusted to remove the coke from the surface of the catalyst particles, forming regenerated catalyst particles.

The regenerated catalyst particles in the combustion zone 180 can enter the regeneration zone 190 where the one or more doping agents can be added either neat via line 187, or mixed with a supplemental fuel via line 188. The one or more doping agents can be dispersed across the surface of the catalyst particles, thereby forming doped catalyst particles which can be recycled from the regeneration zone 190 to the riser 120 via line 195.

Figure 3:
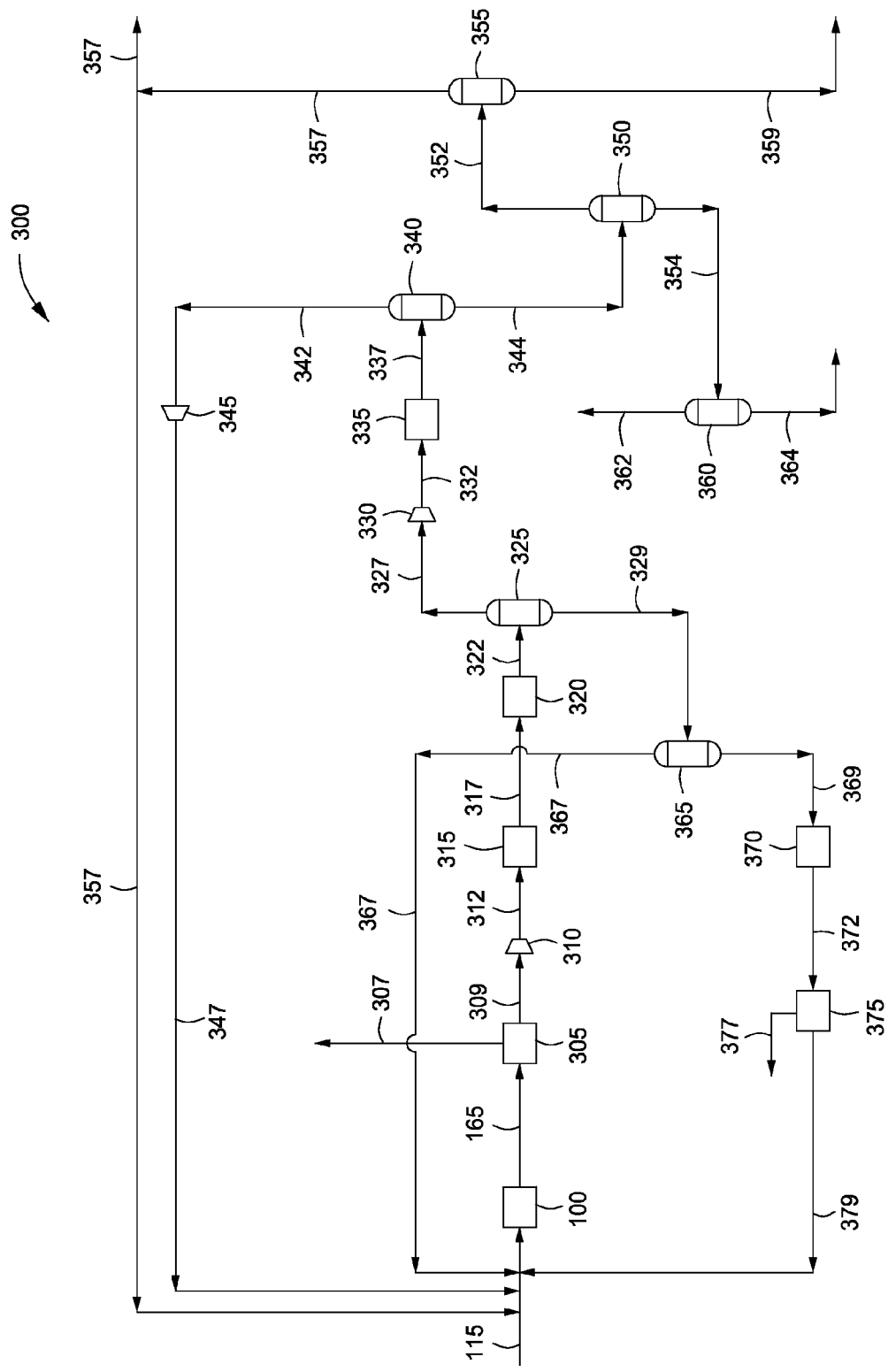
FIG. 3 depicts an illustrative system for producing one or more olefins according to one or more embodiments described.

FIG. 3 depicts an illustrative system 300 for producing one or more olefins according to one or more embodiments. In one or more embodiments, the feedstock via line 115 can be cracked or selectively separated within one or more crackers 100 to provide the first product via line 165, containing naphtha, propylene, ethylene, butane, mixtures thereof and combinations thereof. The first product in line 165 can be fractionated and/or purified using one or more fractionators 305, treating units 315, drying units 320, and separators 325, 340, 350, 355, 360, and 365 to provide multiple products, including propylene, ethylene, propane, and ethane. One or more products, including methane, ethylene, and heavier $C_4$-$C_6$ hydrocarbons can be internally recycled to the one or more crackers 100.

In one or more embodiments, the first product via line 165 can exit the one or more crackers 100 at a temperature of about 425° C. (800° F.) to about 680° C. (1,250° F.), about 450° C. (840° F.) to about 640° C. (1,180° F.), or about 480° C. (900° F.) to about 595° C. (1,100° F.). The first product via line 165 can include about 40% wt, 50% wt, or 60% wt $C_2$-$C_{10}$ hydrocarbons. In one or more embodiments, the first product via line 165 can include from about 5% wt to about 10% wt $C_2$, from about 10% wt to about 30% wt $C_3$, from about 10% wt to about 30% wt $C_4$, and from about 40% wt to about 90% wt $C_5$ and heavier hydrocarbons.

In one or more embodiments, the crackers 100 can be any system, device or combination of systems or devices suitable for catalytic cracking of one or more hydrocarbons. For example, each cracker 100 can be a catalytic cracker, or a fluidized catalytic cracker. A suitable catalytic cracker and/or fluidized catalytic cracker ("FCC") can employ any catalyst useful in catalytic cracking including, but not limited to, zeolytic and shape selective zeolytic catalysts. In one or more specific embodiments a stacked separator/regenerator FCC can be used. In one or more embodiments, one or more doping agents can be added to the catalyst during regeneration as described in reference to FIGS. 1 and 2. In one or more embodiments, the catalyst-to-oil ratio can be from about 5:1 to about 70:1; from about 8:1 to about 25:1; or from about 12:1 to about 18:1.

In one or more embodiments, the first product via line 165 can be selectively separated using one or more fractionators 305 to provide a naphthenic mixture via line 307 and an olefinic mixture via line 309. In one or more embodiments, the olefinic mixture can include a major portion of one or more $C_2$-$C_{10}$ olefins and a minor portion of one or more $C_2$-$C_{10}$ paraffins. In one or more embodiments, the naphthenic mixture can include $C_7$-$C_{12}$ hydrocarbons, one or more light naphthas and/or one or more heavy naphthas. For example, the naphthenic mixture can include from about 10% wt to about 40% wt $C_7$, from about 10% wt to about 40% wt $C_8$, from about 5% wt to about 20% wt $C_6$, and from about 5% wt to about 20% wt $C_{10}$-$C_{12}$ hydrocarbons.

In one or more embodiments, the olefinic mixture via line 309 can include about 30% wt, 40% wt, or 50% wt $C_4$-$C_{10}$ olefins. In one or more embodiments, the olefinic mixture can include from about 10% wt to about 50% wt $C_4$, from about 10% wt to about 50% wt $C_5$, from about 5% wt to about 20% wt $C_6$, and from about 5% wt to about 20% wt $C_7$ and heavier hydrocarbons. In one or more embodiments, the pressure of the olefinic mixture exiting the fractionator 305 can range from about 100 kPa (0 psig) to about 1000 kPa (145 psig).

In one or more embodiments, the olefinic mixture via line 309 can be compressed using one or more compressors 310 to provide a compressed olefinic mixture via line 312. Compressing the olefinic mixture can facilitate the removal of oxygenates, acid gases, water, or any combination thereof from the hydrocarbons from the compressed olefinic mixture in line 312. The compressed olefinic mixture in line 312 can exit the one or more compressors 310 at a pressure ranging from about 100 kPa (0 psig) to about 5,000 kPa (725 psig), about 100 kPa (0 psig) to 3,000 kPa (430 psig), or about 100 kPa (0 psig) to 1,000 kPa (145 psig). In one or more embodiments, the compressed olefinic mixture can be at a temperature of from about 40° C. (100° F.) to about 300° C. (570° F.).

In one or more embodiments, the compressed olefinic mixture in line 312 can be treated in the one or more treating units 315 to remove oxygenates, acid gases, water, or any combination thereof to provide a treated olefinic mixture via line 317. In one or more embodiments, the treated olefinic mixture via line 317 can include less than about 500 ppmv hydrogen sulfide ("$H_2S$"), less than about 50 ppmv $H_2S$, or less than about 1 ppmv $H_2S$. In one or more embodiments, the treated olefinic mixture can include less than about 500 ppmv carbon dioxide ("$CO_2$"); less than about 100 ppmv $CO_2$; or less than about 50 ppmv $CO_2$. In one or more embodiments, the treating unit 315 can include any system or device or combination of systems and/or devices suitable for removing oxygenates, acid gases, water, derivatives thereof, mixtures thereof, which are well known in the art of hydrocarbon refining.

The treated olefinic mixture via line 317 can be dried using one or more drying units 320, providing a dried olefinic mixture via line 322. The dried olefinic mixture in line 322 can include less than 100 ppmv water; less than 10 ppmv water; or less than 0.1 ppmv water. The drying unit 320 can include any system or device or combination of systems and/or devices suitable for removing water from a hydrocarbon to provide a dried olefinic mixture via line 322. For example, the drying unit 320 can include systems that use desiccants, solvents, or any combination thereof for removing water from a hydrocarbon.

In one or more embodiments, the dried olefinic mixture via line 322 can be introduced to one or more separators ("depropanizer") 325 and selectively separated therein to provide an overhead containing $C_3$ and lighter hydrocarbons via line 327, and a bottoms containing $C_4$ and heavier hydrocarbons via line 329. In one or more embodiments, the $C_3$ and lighter hydrocarbons via line 327 can include about 90% wt, 95% wt, or 99% Wt $C_3$ and lighter hydrocarbons. The overhead in line 327 can include from about 10% wt up to about 40% wt $C_2$, from about 20% wt up to about 70% wt $C_3$, and from about 0.1% wt to about 1% wt hydrogen ("$H_2$"). In one or more embodiments, the overhead in line 327 can exit the de-propanizer 325 at pressures ranging from about 500 kPa to about 2500 kPa. In one or more embodiments, the pressure of the overhead in line 327 can range from about 500 kPa (60 psig) to about 1,000 kPa (130 psig).

In one or more embodiments, the bottoms in line 329 can include $C_4$ and heavier hydrocarbons. In one or more embodiments, the bottoms in line 329 can include about 90% wt, 95% wt, or 99% wt $C_4$-$C_{10}$. In one or more embodiments, the $C_4$ and heavier hydrocarbons can range from about 30% wt to about 80% wt $C_4$, from about 5% wt to about 30% wt $C_5$, from about 5% wt to about 20% wt $C_6$, and from about 5% wt to about 20% wt $C_7$ and heavier hydrocarbons.

In one or more embodiments, the one or more de-propanizers 325 can include, but are not limited to, a column containing internal components, as well as one or more condensers and/or reboilers. In one or more embodiments, the one or more de-propanizers 325 can include packing media to facilitate the selective separation of $C_3$ and lighter hydrocarbons from the $C_4$ and heavier hydrocarbons. For example, each de-propanizer 325 can include one or more saddles, balls, irregular sheets, tubes, spirals, trays, and/or baffles. In one or more embodiments, the operating pressure of the de-propanizer 325 can range from about 500 kPa (60 psig) to about 2,500 kPa (350 psig), and the operating temperature of the de-propanizer 325 can range from about −60° C. (−75° F.) to about 100° C. (210° F.).

The bottoms via line 329 can be introduced to one or more separators ("gasoline splitters") 365 and selectively separated therein to provide an overhead containing $C_4$-$C_6$ hydrocarbons via line 367, and a bottoms containing $C_7$ and heavier hydrocarbons via line 369. In one or more embodiments, the overhead via line 367 can include butanes and isobutanes. For example, the overhead via line 367 can include from about 50% wt to about 95% wt butanes. In one or more embodiments, the overhead via line 367 can include from about 10% wt to about 50% wt isobutanes. In one or more embodiments, the overhead via line 367 can include from about 10% wt to about 50% wt $C_4$ olefins, from about 5% wt to about 30% wt $C_5$ olefins, and from about 5% wt to about 20% wt $C_6$ olefins.

In one or more embodiments, all or any portion of the overhead in line 367 can be recycled to the cracker 100. For example, from about 10% wt to about 100% wt, from about 20% wt to about 100% wt, from about 30% wt to about 100% wt, from about 40% wt to about 100% wt, or from about 45% wt to about 100% wt of the overhead in line 367 can be recycled to the cracker 100.

In one or more embodiments, the gasoline splitter 365 can include any device, system or combination of devices and/or systems suitable for selectively separating a hydrocarbon mixture to provide the overhead via line 367 containing the $C_4$-$C_6$ hydrocarbons, and the bottoms via line 369 containing the $C_7$ and heavier hydrocarbons. In one or more embodiments, the gasoline splitter 365 can include, but is not limited to, a column containing internal components, as well as one or more condensers and/or reboilers. In one or more embodiments, the gasoline splitter 365 can include packing media to facilitate the selective separation of $C_6$ and lighter hydrocarbons from $C_7$ and heavier hydrocarbons. For example, each gasoline splitter 365 can include saddles, balls, irregular sheets, tubes, spirals, trays, and/or baffles. In one or more embodiments, the operating pressure of the gasoline splitter 365 can range from about 100 kPa (0 psig) to about 2,500 kPa (350 psig), and temperature can range from about 20° C. (70° F.) to about 400° C. (750° F.).

In one or more embodiments, all or any portion of the $C_7$ and heavier hydrocarbons in line 369 can be introduced to one or more gasoline hydrotreaters 370 and stabilized therein to provide a treated gasoline via line 372. In one or more embodiments, the treated gasoline via line 372 can include a minimum of about 70% wt, 80% wt, or 90% wt $C_6$ and heavier hydrocarbons. In one or more embodiments, the treated gasoline via line 372 can include about 75% wt to about 85% wt $C_6$, about 15% wt to about 25% wt $C_7$, or about 5% wt to about 10% wt $C_8$ and heavier hydrocarbons. The gasoline hydrotreater 370 can include any system or device or combination of systems and/or devices suitable for stabilizing a mixed hydrocarbon. In one or more embodiments, the hydrotreater 370 can include a system that stabilizes gasoline by treating with hydrogen.

All or any portion of the treated gasoline via line 372 can be introduced to one or more BTX units 375 to provide one or more aromatics including, but not limited to, benzene, toluene, xylene, or any combination thereof ("aromatics"), via line 379, and a raffinate via line 377. In one or more embodiments, the aromatics via line 379 can include about 40% wt, 50% wt, 60% wt, 70% wt, or 80% wt BTX. The BTX can include from about 10% wt to about 40% wt benzene, from about 20% wt to about 60% wt toluene, and from about 10% wt to about 40% wt xylene. In one or more embodiments, at least a portion of the aromatics via line 379 can be combined with the feedstock line 115 and recycled to the one or more crackers 100. Although not shown in FIG. 3, in one or more embodiments, at least a portion of the aromatics via line 379 can be directly recycled to the cracker 100. For example, at least about 10% wt, 20% wt, 30% wt, or 40% wt of the aromatics via line 379 can be recycled to the one or more crackers 100, either directly or via line 115. In at least one specific embodiment, about 10% wt, 15% wt, or 20% wt of the aromatics via line 379 can be recycled to the cracker 100, either directly or via line 115.

Although not shown, the raffinate via line 377 can be further processed. For example, all or any portion of the raffinate 377 can be directed to a steam pyrolytic cracker (not shown) to recover any olefinic or paraffinic hydrocarbons contained therein.

Returning to the de-propanizer 325, the overhead via line 327 can be compressed using one or more compressors 330 to provide compressed $C_3$ and lighter hydrocarbons via line 332. In one or more embodiments, compressing the $C_3$ and lighter hydrocarbons can facilitate the subsequent separation of the lighter compounds from the $C_3$. The pressure of the compressed $C_3$ and lighter hydrocarbons can range from about 500 kPa (60 psig) to about 3,500 kPa (490 psig), for example.

In one or more embodiments, the compressed $C_3$ and lighter hydrocarbons via line 332 can be cooled using one or more chill trains 335 to provide chilled $C_3$ and lighter hydrocarbons via line 337. The temperature of the chilled $C_3$ and lighter hydrocarbons in line 337 can range from about −40° C. (−40° F.) to about 40° C. (100° F.). In one or more specific embodiments, the chilled $C_3$ and lighter hydrocarbons in line 337 can have a temperature from about −20° C. (−5° F.) to about 5° C. (40° F.).

In one or more embodiments, the chilled $C_3$ and lighter hydrocarbons via line 337 can be selectively separated using one or more separators ("de-methanizers") 340 to provide an overhead via line 342 containing methane, and a bottoms via line 344 containing $C_2$ and $C_3$ hydrocarbons. In one or more embodiments, the overhead via line 342 can include about 70 mol %, 80 mol %, or 90 mol % methane. In one or more embodiments, the bottoms via line 344 can include from about 20% wt to about 50% wt $C_2$ and from about 40% wt to about 80% wt $C_3$. In one or more embodiments, the overhead via line 342 can include about 50 mol % to about 95 mol % methane. In one or more embodiments, the operating pressure of the de-methanizers 340 can range from about 300 kPa (30 psig) to about 1,000 kPa (130 psig). The $C_2$ and $C_3$ hydrocarbons via line 344 can include up to about 95% wt $C_2$-$C_3$.

In one or more embodiments, all or any portion of the overhead in line 342 can be compressed using one or more compressors 345 to provide compressed methane via line 347, which can be recycled to the one or more crackers 100 via line 115. Although not shown in FIG. 3, in one or more embodiments, all or any portion of the compressed methane via line 347 can be recycled directly to the cracker 100. In one or more embodiments, from about 15% vol to about 35% vol, from about 20% vol to 35% vol, from about 25% vol to 35% vol, or from about 30% vol to 35% vol of the compressed methane via line 347 can be recycled to the cracker 100, either directly or via line 115. The compressed methane exiting the compressor 345 can have temperature ranging from about 25° C. (80° F.) to about 200° C. (390° F.).

In one or more embodiments, the bottoms in line 344 can be introduced to one or more separators ("de-ethanizers") 350 and selectively separated therein to provide an overhead containing a $C_2$ hydrocarbon mixture via line 352, and a bottoms containing a $C_3$ hydrocarbon mixture via line 354. In one or more embodiments, the overhead 352 can include about 90 mol %, 95 mol %, or 99 mol % $C_2$ hydrocarbon mixture. In one or more embodiments, the overhead in line 352 can contain from about 5 mol % to about 70 mol % ethane and from about 30 mol % to about 95 mol % ethylene. In one or more embodiments, the bottoms in line 354 can include about 90 mol %, 95 mol %, or 99 mol % $C_3$ hydrocarbons. In one or more embodiments, the $C_3$ hydrocarbons in line 354 can include from about 5 mol % to about 30 mol % propane and from about 70 mol % to about 95 mol % propylene. In one or more embodiments, the operating pressure of the de-ethanizer 350 can range from about 500 kPa (60 psig) to about 2,500 kPa (350 psig), and the temperature can range from about −80° C. (−110° F.) to about 100° C. (210° F.).

In one or more embodiments, at least a portion of the $C_2$ hydrocarbon mixture in the overhead in line 352 can be introduced to one or more separators ("C2 splitters") 355 and selectively separated therein to provide an ethylene product via line 357 and an ethane product via line 359. In one or more embodiments, the ethane product via line 359 can include about 90 mol %, about 95 mol %, about 99 mol %; or about 99.9 mol % ethane. In one or more embodiments, the ethylene product via line 357 can include about 90 mol %, about 95 mol %, about 99 mol %, or about 99.9 mol % ethylene.

In one or more embodiments, all or any portion of the ethylene product via line 357 can be recycled to the cracker 100. Recycling at least a portion of the ethylene product can suppress propylene production in the one or more crackers 100, thereby increasing the yield of ethylene in the first product via line 165. In one or more embodiments, from about 10% vol to about 60% vol; about 20% vol to about 60% vol; about 30% vol to about 60% vol; about 40% vol to about 60% vol; or about 50% vol to about 60% vol of the ethylene product via line 357 can be recycled to the one or more crackers 100. In one or more embodiments, from about 60% vol to about 99% vol, from about 70% vol to about 95% vol, or from about 80% vol to about 90% vol of the ethylene product can be recycled to the one or more crackers 100. In one or more embodiments, at least a portion of the ethylene present in line 357 can be removed as a finished product.

In one or more embodiments, the C2 splitter 355 can be any device, system or combination of devices and/or systems suitable for selectively separating a hydrocarbon mixture to provide the ethylene product via line 357 and the ethane product via line 359. In one or more embodiments, the C2 splitter 355 can include, but is not limited to, a column containing internal components, condensers and/or reboilers. In one or more embodiments, the operating pressure of the C2 splitter 355 can range from about 500 kPa (60 psig) to about 2,500 kPa (350 psig). In one or more embodiments the operating temperature of the C2 splitter can range from about −80° C. (−110° F.) to about 100° C. (210° F.).

In one or more embodiments, the bottoms via line 354, containing $C_3$ hydrocarbons, can be introduced to one or more C3 splitters 360 and selectively separated therein to provide a propylene product ("second product") via line 362 and a propane product via line 364. In one or more embodiments, the propane product in line 364 can contain about 90 mol %, 95 mol %, 99 mol %, or 99.9 mol % propane. In one or more embodiments, the propylene product via line 362 can include from about 60% wt to about 99.9% wt propylene.

The C3 splitter 360 can be any device, system or combination of systems and/or devices suitable for selectively separating the $C_3$ hydrocarbon mixture to provide the propylene product via line 362 and the propane product via line 364. In one or more embodiments, the C3 splitter 360 can include, but is not limited to, a column containing internal components, as well as one or more condensers and/or reboilers. In one or more embodiments, the operating pressure of the C3 splitter 360 can range from about 500 kPa (60 psig) to about 2,500 kPa (350 psig), In one or more embodiments the operating temperature of the C3 splitter can range from about −100° C. (−150° F.) to about 100° C. (210° F.).

Figure 4:
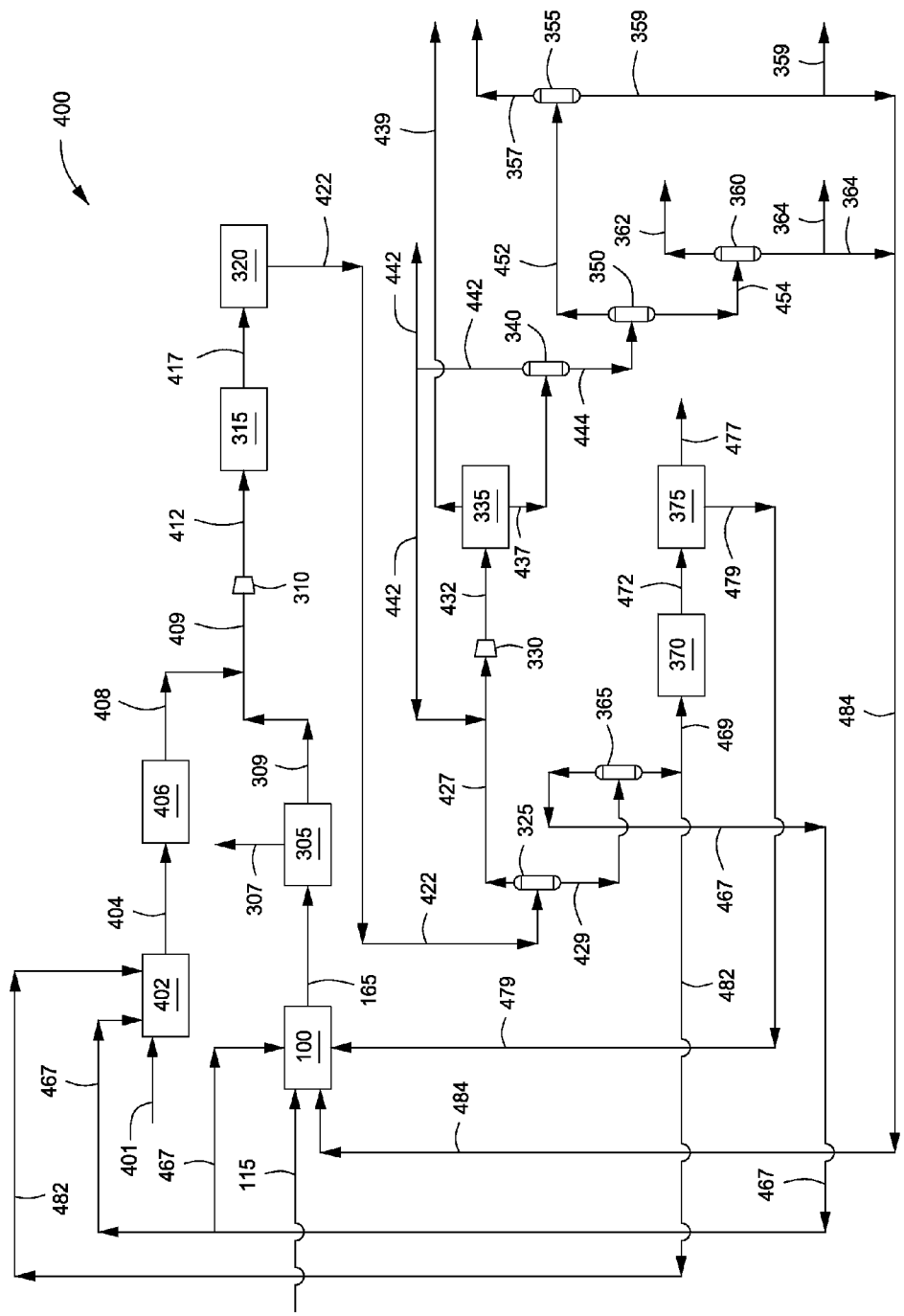
FIG. 4 depicts another illustrative system for producing one or more olefins according to one or more embodiments described.

FIG. 4 depicts another illustrative system 400 for producing one or more olefins according to one or more embodiments. As depicted, the feedstock via line 115 can be introduced to the one or more crackers 100 and cracked therein to provide the first product via line 165. The first product via 165 can be introduced to the one or more fractionators 305 to provide the olefinic mixture via line 309 and the naphthenic mixture via line 307. Similarly, one or more hydrocarbons ("refinery hydrocarbons") can be introduced via line 401 to one or more crackers 402 and cracked therein to provide product via line 404 containing ethylene, propylene, ethane, propane and/or butane. In one or more embodiments the product in line 404 can be introduced to one or more quench columns 406 to provide quenched product via line 408. The quenched product in line 408 can be combined with the olefinic mixture in line 309 to provide a combined hydrocarbon mixture via line 409.

In one or more embodiments, each cracker 402 can be a fluid catalytic riser type reactor containing one or more risers or cracking zones suitable for cracking and/or selectively separating a refinery hydrocarbon. As used herein, the term "refinery hydrocarbon" refers to gas oils, full range gas oils, resids, derivatives thereof, and/or mixtures thereof. In one or more embodiments, at least two fluid catalytic crackers 402 can operate in parallel or series. The temperature of the riser or cracking zone of the fluid catalytic cracker 402 can range from about 400° C. to about 600° C.

In one or more embodiments, the hydrocarbon mixture via line 409 can be compressed using one or more compressors 310 to provide a compressed mixture via line 412 which can be treated using one or more treating units 315 to provide a treated mixture via line 417. In one or more embodiments, the treated mixture can be dried using one or more drying units 320 to provide a dried mixture via line 422. The dried mixture via line 422 can be introduced to one or more de-propanizers 325 and selectively separated therein to provide an overhead 427 containing $C_3$ and lighter hydrocarbons and a bottoms 429 containing $C_4$ and heavier hydrocarbons.

In one or more embodiments, the $C_4$ and heavier hydrocarbons via line 429 can be introduced to one or more gasoline splitters 365 and selectively separated therein to provide an overhead 467 containing $C_4$-$C_6$ hydrocarbons and a bottoms 469 containing $C_7$ and heavier hydrocarbons. In one or more embodiments, at least a portion of the $C_4$-$C_6$ hydrocarbons in line 467 can be recycled to the cracker 100 and/or hydrocarbon feed in line 115 (not shown). In one or more embodiments, about 5% wt, about 15% wt, about 25% wt, about 35% wt, about 45% wt, about 55% wt, or about 65% wt of the $C_4$-$C_6$ hydrocarbons via line 467 can be recycled to the cracker 100 and/or hydrocarbon feed in line 115.

In one or more embodiments, at least a portion of the $C_4$-$C_6$ hydrocarbons via line 467 can be recycled to the cracker 402 and/or refinery feed 401 (not shown). For example, from about 55% wt to about 95% wt; about 55% wt to about 65% wt; about 65% wt to about 75% wt; about 75% wt to about 85% wt; or about 85% wt to about 95% wt of the $C_4$-$C_6$ hydrocarbons via line 467 can be recycled to the cracker 402 and/or refinery feed 401 (not shown). In one or more embodiments, from about 10% wt to about 20% wt; about 20% wt to about 30% wt; about 30% wt to about 40% wt; or about 40% wt to about 50% wt of the $C_4$-$C_6$ hydrocarbons via line 467 can be recycled to the cracker 402 and/or refinery feed 401 (not shown).

In one or more embodiments, at least a portion of the $C_4$-$C_6$ hydrocarbons via line 467 can be recycled to the cracker 100 and at least a portion to the cracker 402. In one or more embodiments, about 10% wt to about 60% wt, about 10% wt to about 35% wt, about 25% wt to about 45% wt, or about 35% wt to about 60% wt of the $C_4$-$C_6$ hydrocarbons via line 467 can be recycled to the cracker 100 with the balance recycled to the cracker 402. In one or more embodiments, from about 25% wt to about 99% wt, from about 25% wt to about 55% wt, from about 45% wt to about 65% wt, from about 55% wt to about 85% wt, or from about 65% wt to 100% wt of the $C_4$-$C_6$ hydrocarbons via line 467 can be recycled to the cracker 100 with the balance to the cracker 402. Recycling at least a portion of the $C_4$-$C_6$ hydrocarbons to the cracker 100 can increase the production of aromatic BTX. Recycling at least a portion of the $C_4$-$C_6$ hydrocarbons via line 467 to the cracker 402 can increase the production of propylene by increasing the concentration of $C_4$ and higher compounds in the cracker 402.

In one or more embodiments, the gasoline splitter bottoms via line 469, containing $C_7$ and heavier hydrocarbons, can be stabilized using one or more gasoline hydrotreaters 370 to provide a treated gasoline via line 472. In one or more embodiments, at least a portion of the $C_7$ and heavier hydrocarbons in line 469 can be recycled to the second cracker 402 via recycle line 482. In one or more embodiments, about 10% wt to about 20% wt, about 15% wt to about 35% wt, about 30% wt to 55% wt, about 50% wt to about 75% wt, or about 65% wt to about 80% wt of the $C_7$ and heavier hydrocarbons via line 469 can be recycled to the second cracker 402 via recycle line 482. Recycling at least a portion of the $C_7$ and heavier hydrocarbons to the second cracker 482 can increase the production of ethylene.

The treated gasoline via line 472 can be introduced to one or more BTX units 375 and selectively separated therein to provide aromatics, including, but not limited to, benzene, toluene, xylene, mixtures thereof, or combinations thereof via line 477, and a raffinate via line 479. In one or more embodiments, the aromatics content of the raffinate in line 479 can be less than about 10% wt, 5% wt, or 1% wt BTX. In one or more embodiments, all or any portion of the raffinate via line 479 can be recycled to the cracker 100. For example, at least 20% wt, 30% wt, 40% wt, or 50% wt of the raffinate in line 479 can be recycled to the cracker 100. In one or more embodiments, at least 70% wt, 80% wt, or 90% wt of the raffinate in line 479 can be recycled to the cracker 100.

Returning to the de-propanizer 325, in one or more embodiments, the overhead, containing $C_3$ and lighter hydrocarbons in line 427 can be compressed using one or more compressors 330 to provide compressed $C_3$ and lighter hydrocarbons via line 432. In one or more embodiments, the compressed $C_3$ and lighter hydrocarbons via line 432 can be chilled using one or more chill trains 335 to provide an overhead containing hydrogen via line 439 and a bottoms containing $C_3$ and lighter hydrocarbons via line 437. In one or more embodiments, chilling the compressed $C_3$ and lighter hydrocarbons can further facilitate the separation of hydrogen and other non-condensables via line 439 from the $C_3$ and lighter hydrocarbons via line 437.

In one or more embodiments, the $C_3$ and lighter hydrocarbons via line 437 can be selectively separated using one or more de-methanizers 340 to provide an overhead containing methane via line 442 and a bottoms containing $C_2$ and $C_3$ hydrocarbons via line 444. In one or more embodiments, all or any portion of the methane via line 442 can be recycled to the one or more compressors 330. Recycling at least portion of the methane via line 442 can auto-refrigerate the compressed $C_3$ and lighter hydrocarbons via line 427 thereby improving the recovery of olefins, and increasing the propylene yield in the converted propylene production process.

In one or more embodiments, the $C_2$ and $C_3$ hydrocarbons via line 444 can be selectively separated using one or more de-ethanizers 350 to provide an overhead containing a $C_2$ hydrocarbon mixture via line 452 and a bottoms containing a $C_3$ hydrocarbon mixture via line 454. In one or more embodiments, one or more C2 splitters 355 can be used to selectively separate the $C_2$ hydrocarbon mixture via line 452 to provide an ethylene product via line 357 and an ethane product via line 359. One or more C3 splitters 360 can be used to selectively separate the $C_3$ hydrocarbon mixture via line 454 to provide a propylene product via line 362 and a propane product via line 364.

In one or more embodiments, all or any portion of the ethane product via line 359 and propane product via line 364 can be recycled to the one or more crackers 100 via recycle line 484. For example, from about 60% vol to about 100% vol; from about 70% vol to about 100% vol; from about 80% vol to about 100% vol; or from about 90% vol to about 100% vol of the ethane product via line 359 and from about 70% vol to about 100% vol, from about 80% vol to about 100% vol, or from about 90% vol to about 100% vol of the propane product via line 364 can be recycled to the one or more crackers 100 via line 484. In one or more embodiments, from about 15% vol to about 55% vol, from about 25% vol to about 55% vol, from about 35% vol to about 55% vol, or from about 45% vol to about 55% vol of the propane product via line 364 can be recycled to the one or more crackers 100. In at least one specific embodiment, from about 15% vol to about 45% vol, from about 25% vol to about 45% vol, or from about 35% vol to about 45% vol of the ethane product via line 359 can be recycled to the cracker 100.

Figure 5:
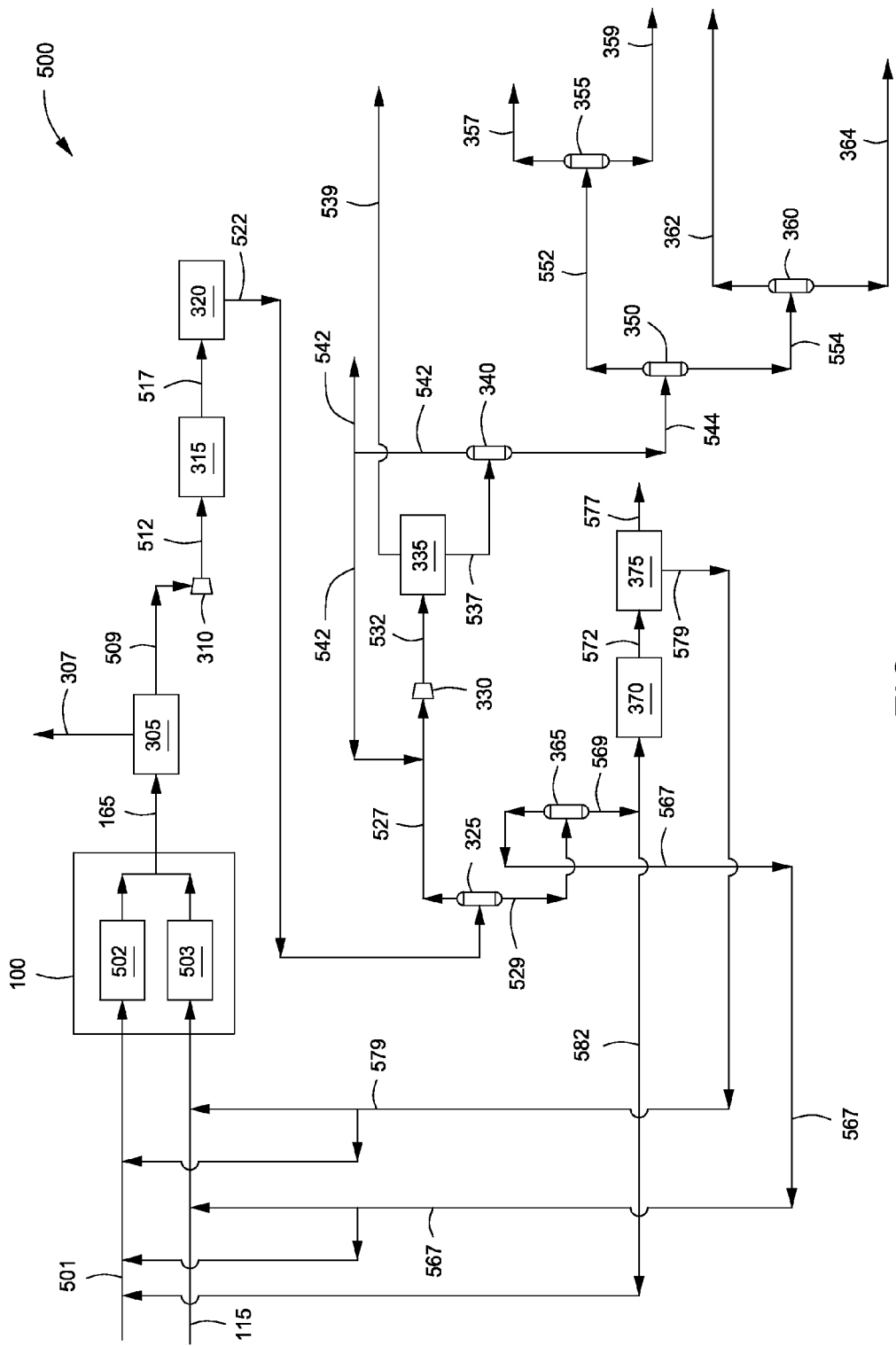
FIG. 5 depicts another illustrative system for producing one or more olefins according to one or more embodiments described.

FIG. 5 depicts another illustrative system 500 for producing one or more olefins according to one or more embodiments. In one or more embodiments, each cracker 100 can include two or more risers or zones 502, 503 each independently operated at conditions sufficient to crack or otherwise selectively separate different feeds or cuts into one or more olefins. In one or more embodiments, the refinery hydrocarbon (defined above) via line 501 can be introduced to the riser or first zone 502 and the feedstock via line 115 can be introduced to the second riser or cracking zone 503. The effluents from each riser or cracking zone 502, 503 can be combined, forming the hydrocarbon mixture via line 165. In one or more embodiments, the hydrocarbon mixture can be fractionated and purified using the one or more fractionators 305, purifiers 315, 320 and columns 325, 365, 340, 350, 355, and 360, all as described above, to provide multiple products including propylene, ethylene, propane and ethane.

In one or more embodiments, the first product via line 165 can be introduced to the one or more fractionators 305 and selectively separated therein to provide a naphthenic mixture via line 307 and an olefinic mixture via line 509. In one or more embodiments, the naphthenic mixture can include, but is not limited to light naphthas, heavy naphthas, napthenic compounds, derivatives thereof, mixtures thereof, or combinations thereof. The olefinic mixture via line 509 can be compressed using the one or more compressors 310 to provide a compressed olefinic mixture via line 512 which can be treated using the one or more treating units 315 to provide a treated olefinic mixture via line 517. The treated olefinic mixture can be introduced to the one or more drying units 320 to provide dried olefinic mixture via line 522.

In one or more embodiments, the dried olefinic mixture via line 522 can be introduced to the one or more de-propanizers 325 and selectively separated therein to provide an overhead containing $C_3$ and lighter hydrocarbons via line 527, and a bottoms containing $C_4$ and heavier hydrocarbons via line 529. In one or more embodiments, the $C_4$ and heavier hydrocarbons via line 529 can be introduced to the one or more gasoline splitters 365 and selectively separated therein to provide an overhead containing $C_4$-$C_6$ hydrocarbons via line 567 and a bottoms containing $C_7$ and heavier hydrocarbons via line 569.

In one or more embodiments, at least a portion of the $C_4$-$C_6$ hydrocarbons via line 567 can be recycled to the first riser or cracking zone 502 and/or the second riser or cracking zone 503. For example, about 10% wt to about 60% wt, about 10% wt to about 35% wt, about 25% wt to about 45% wt, or about 35% wt to about 60% wt of the $C_4$-$C_6$ hydrocarbons via line 567 can be recycled to the first riser or cracking zone 502 with the balance recycled to the second riser or cracking zone 503. In one or more embodiments, from about 25% wt to about 100% wt, 25% wt to about 55% wt, about 45% wt to about 65% wt, about 55% wt to about 85% wt, or about 65% wt to 99% wt of the $C_4$-$C_6$ hydrocarbons via line 567 can be recycled to the first riser or cracking zone 502 with the balance to the second riser or cracking zone 503. Recycling at least a portion of the $C_4$-$C_6$ hydrocarbons via line 567 to the first riser or cracking zone 502 can increase the production of the aromatics (i.e. BTX). Recycling at least a portion of the $C_4$-$C_6$ hydrocarbons via line 567 to the second riser or cracking zone 503 can increase the production of propylene.

In one or more embodiments, at least a portion of the $C_7$ and heavier hydrocarbons via line 569 can be recycled via line 582 to the first riser or cracking zone 502. In one or more embodiments, from about 10% wt to about 20% wt; about 15% wt to about 35% wt; about 30% wt to 55% wt; about 50% wt to about 75% wt; or about 65% wt to about 80% wt of the $C_7$ and heavier hydrocarbons in line 569 can be recycled to the first riser or cracking zone 502 via recycle line 582. Recycling at least a portion of the $C_7$ and heavier hydrocarbons via line 582 can increase the production of ethylene by increasing the concentration of heavy hydrocarbons in the first riser or cracking zone 502.

In one or more embodiments, the $C_7$ and heavier hydrocarbons via line 569 can be stabilized using the one or more gasoline hydrotreaters 370 to provide a treated gasoline via line 572. The treated gasoline via line 572 can be selectively separated using the one or more BTX units 375 to separate the aromatics via line 577 from a raffinate via line 579.

In one or more embodiments, at least a portion of the raffinate via line 579 can be recycled to the second riser or cracking zone 503. In one or more embodiments, the raffinate via line 579 can be lean in aromatics. For example, the raffinate via line 579 can include less than about 10% wt, 5% wt, or 1% wt BTX. In one or more embodiments, at least 70% wt, 80% wt, or 90% wt of the raffinate via line 579 can be recycled to the second riser or cracking zone 503 with the balance to the first riser or cracking zone 502. In one or more embodiments, at least 20% wt, 30% wt, 40% wt, or 50% wt of the raffinate via line 579 can be recycled to the first riser or cracking zone 502. In one or more embodiments, at least 20% wt, 30% wt, 40% wt, or 50% wt of the raffinate via line 579 can be recycled to the second riser or cracking zone 503 with the balance to the first riser or cracking zone 502. In one or more embodiments, at least 70% wt, 80% wt, or 90% wt of the raffinate via line 579 can be recycled to the second riser or cracking zone 503 with the balance to the first riser or cracking zone 502.

Although not shown in FIG. 5, in one or more embodiments, all or any portion of the aromatics via line 577 can be recycled to the first riser or cracking zone 502. For example, at least 20% wt, 40% wt, 60% wt, 80% wt, or 90% wt of the aromatics via line 577 can be recycled to the first riser or cracking zone 502.

Returning to the de-propanizer 325, in one or more embodiments, the $C_3$ and lighter hydrocarbons via line 527 can be compressed using the one or more compressors 330 to provide compressed $C_3$ and lighter hydrocarbons via line 532. The compressed $C_3$ and lighter hydrocarbons via line 532 can be chilled and separated using one or more chill trains 335 to provide an overhead containing hydrogen and non-condensable gases, mixtures thereof and combinations thereof via line 539, and a bottoms containing $C_3$ and lighter hydrocarbons via line 537.

In one or more embodiments, the $C_3$ and lighter hydrocarbons via line 537 can be introduced to the one or more de-methanizers 340 and selectively separated therein to provide an overhead containing methane via line 542 and a bottoms containing $C_2$ and $C_3$ hydrocarbons via line 544. In one or more embodiments, all or any portion of the methane via line 542 can be recycled to the inlet of the one or more compressors 330. Recycling at least portion of the methane via line 542 autorefrigerates the compressed $C_3$ and lighter hydrocarbons in line 527 thereby improving the recovery of olefins and increasing the propylene yield in the converted propylene production process.

In one or more embodiments, the $C_2$ and $C_3$ hydrocarbons via line 544 can be introduced to the one or more de-ethanizers 350 and selectively separated therein to provide an overhead containing a $C_2$ hydrocarbon mixture via line 552 and a bottoms containing a $C_3$ hydrocarbon mixture via line 554. In one or more embodiments, the $C_2$ hydrocarbon mixture via line 552 can be introduced to the one or more C2 splitters 355 and selectively separated therein to provide an ethylene product via line 357 and an ethane product via line 359. The one or more C3 splitters 360 can be used to selectively separate the $C_3$ hydrocarbon mixture via line 554 to provide the propylene product via line 362 and the propane product via line 364.

Figure 6:
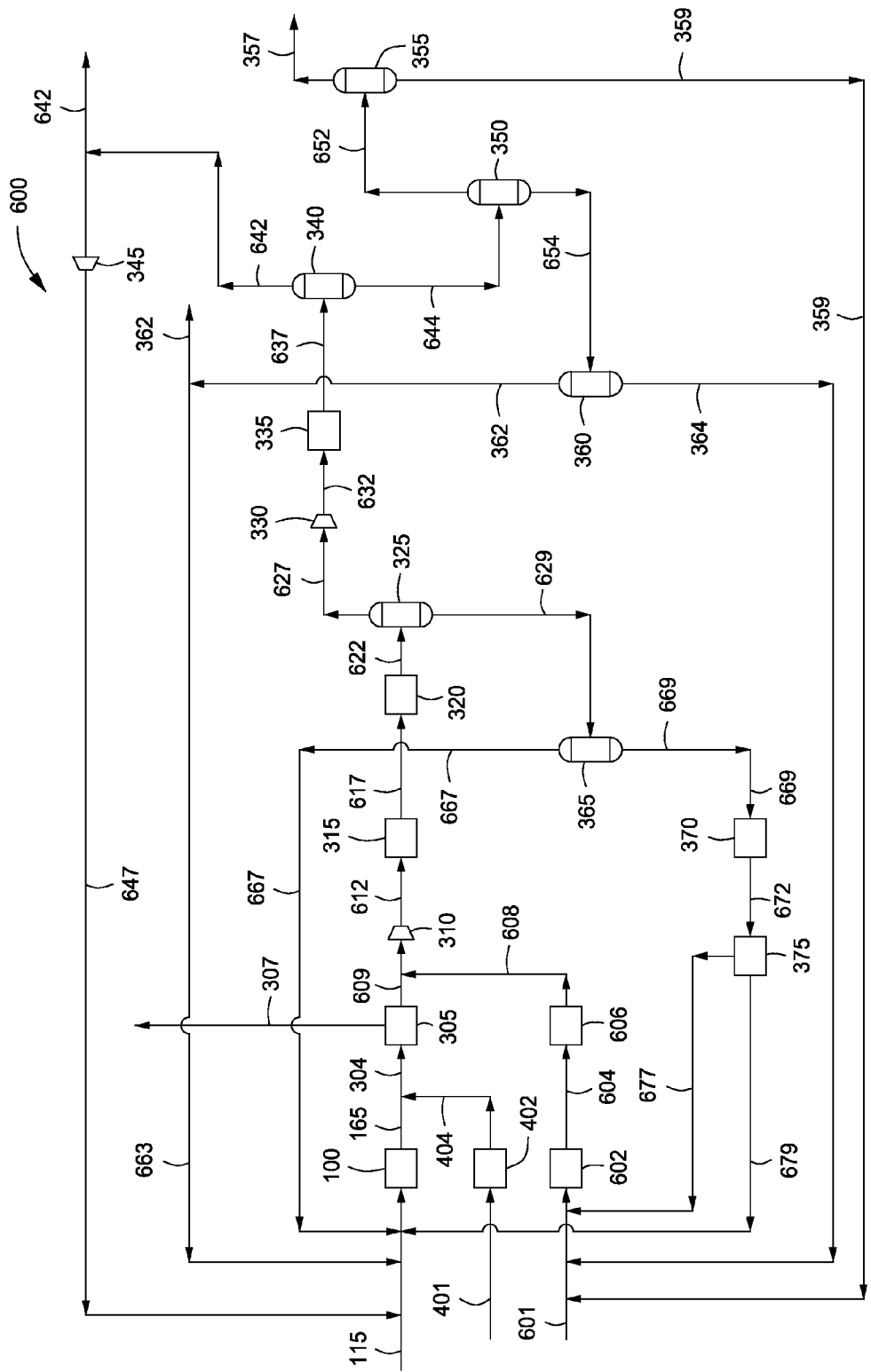
FIG. 6 depicts another illustrative system for producing one or more olefins according to one or more embodiments described.

FIG. 6 depicts another illustrative system 600 for producing one or more olefins according to one or more embodiments. In one or more embodiments, the feedstock via line 115 can be introduced to the one or more crackers 100 and cracked therein to provide the first product via line 165. In one or more embodiments, one or more refinery hydrocarbons and/or light hydrocarbons can be introduced via line 401 to a fluid catalytic cracker ("FCC") 402 and cracked therein to provide a cracked hydrocarbon via line 404. In one or more embodiments, one or more alkanes can be introduced via line 601 to one or more steam pyrolytic crackers 602 to provide an effluent ("cracked alkanes") via line 604. The cracked alkanes via line 604 can be cooled using one or more quench columns 606 to provide a cooled effluent via 608.

Although not shown in FIG. 6, in one or more embodiments, one or more mixed hydrocarbon feeds can be introduced to one or more pre-fractionators. Within the one or more pre-fractionators, the mixed hydrocarbon feed can be fractionated or otherwise selectively separated to provide at least a portion of the feedstock in line 115, at least a portion of the one or more refinery hydrocarbons and/or light hydrocarbons via line 401, and/or at least a portion of the one or more alkanes via line 601.

In one or more embodiments, the first product via line 165 and the cracked hydrocarbon via line 404 can be combined to provide a second hydrocarbon mixture via line 304. In one or more embodiments, the hydrocarbon mixture in line 304 can be fractionated using one or more fractionators 305 to provide an olefinic mixture via 609 and a naphthenic mixture via line 307. The olefinic mixture via 609 can be combined with the quenched effluent via 608 and purified using the one or more purifiers 315, 320 and columns 325, 365, 340, 350, 355, and 360 to provide multiple products including propylene, ethylene, propane and ethane. Heavier $C_4$-$C_6$ hydrocarbons, separated from the finished products, can be recycled to the one or more crackers 100, 402, 602 as depicted in FIG. 6.

In one or more embodiments, the one or more fractionators 305 can remove heavy naphtha, light cycle oil, slurry oil, or any combination thereof from the second hydrocarbon mixture to recover the olefinic mixture via line 609 and the naphthenic mixture via line 307. In one or more embodiments, the olefinic mixture can include one or more $C_2$-$C_{10}$ olefins. In one or more embodiments, the naphthenic mixture via line 307 can include about 40% wt to about 90% wt $C_7$-$C_{12}$ hydrocarbons. In one or more embodiments, the naphtha via line 307 can include from about 5% wt to about 40% wt $C_7$, from about 5% wt to about 40% wt $C_8$, from about 5% wt to about 20% wt $C_4$, or from about 5% wt to about 10% wt $C_{10}$ and heavier hydrocarbons. The olefinic mixture via line 609 can include 20% wt to 90% wt of the one or more $C_2$-$C_{10}$ hydrocarbons. In one or more embodiments, the olefinic mixture can include from about 5% wt to about 30% wt $C_4$, from about 5% wt to about 30% wt $C_5$, from about 5% wt to about 30% wt $C_6$, and from about 5% wt to about 20% wt $C_7$ and heavier hydrocarbons. In one or more embodiments, the olefinic mixture can exit the fractionator 305 at a pressure of about 100 kPa (0 psig) up to about 500 kPa (60 psig).

In one or more embodiments, the refinery and/or light hydrocarbons can be introduced to the one or more fluidized catalytic crackers 402 at a temperature ranging of about 25° C. to about 300° C. In one or more embodiments, the refinery and/or light hydrocarbons can be pre-heated to temperatures ranging from about 25° C. (80° F.) to about 200° C. (390° F.) prior to cracking.

In one or more embodiments, the alkanes introduced via line 601 to the steam pyrolytic cracker 602 can include one or more paraffinic hydrocarbons having two or more carbon atoms. In one or more embodiments, the alkanes can include one or more $C_2$-$C_{12}$ paraffinic hydrocarbons. In one or more embodiments, the one or more alkanes can be introduced to the steam pyrolytic cracker 602 at a temperature of about 25° C. to about 200° C. In one or more embodiments, the one or more alkanes can be introduced to the steam pyrolytic cracker 602 at a pressure of about 100 kPa (0 psig) to about 2,000 kPa (275 psig).

The cracked hydrocarbons via line 404 can include 50% wt, 60% wt, or 70% wt $C_4$-$C_{10}$. In one or more embodiments, the cracked hydrocarbons in line 404 can include from about 1% wt to about 10% wt $C_2$, from about 1% wt to about 20% wt $C_3$, from about 5% wt to about 25% wt $C_4$, from about 5% wt to about 25% wt $C_5$, and from about 30% wt to about 70% wt $C_6$ and heavier hydrocarbons. In one or more embodiments, the cracked hydrocarbons can exit the fluidized catalytic cracker 402 at a temperature of about 400° C. (750° F.) to about 600° C. (1,110° F.).

In one or more embodiments, the alkane feed via line 601 can include methane, ethane, propane, mixtures thereof or combinations thereof. In one or more embodiments, the alkane feed via line 601 can include from about 70% wt, 80% wt, or 90% wt $C_2$-$C_3$ alkanes. In one or more embodiments, the alkane feed via line 601 can be introduced to the convection zone of the steam pyrolytic cracker 602 at a temperature of about 100° C. (210° F.) to about 300° C. (570° F.). The alkane feed can be heated in the convection zone of the steam pyrolytic cracker 602 to a temperature of about 400° C. (750° F.) to about 700° C. (1,290° F.). In one or more embodiments, the alkane feed can be partially vaporized in the convection zone. For example, about 10% wt, 20% wt, 30% wt, 40% wt, or 50% wt of the alkane feed can be vaporized in the convection zone of the steam pyrolytic cracker 602. In one or more embodiments, a minimum of 55% wt, 65% wt, 75% wt, 85% wt, 95% wt, or 100% wt of the alkane feed via line 601 can be vaporized in the convection zone of the steam pyrolytic cracker 602. In one or more embodiments, the quenched effluent in line 608 can include about 20% wt to about 60% wt ethane and about 5% wt to about 30% wt propane.

In one or more embodiments, the quench column 606 can be any device, system or combination of systems and/or devices suitable for reducing the temperature of the cracked hydrocarbon mixture in line 604. In one or more embodiments, reducing the temperature of the cracked hydrocarbon can reduce or stop the rate of hydrocarbon cracking. In one or more embodiments, the quench column 606 can include packing media to provide surface area for the cracked alkanes and a heat transfer medium to make thermal contact. For example, the packing media can include rings, saddles, balls, irregular sheets, tubes, spirals, trays, baffles, or any combination thereof. In one or more embodiments, the cooled hydrocarbons can exit the quench column 606 via line 608 at a temperature from about 25° C. to about 100° C.

In one or more embodiments the cooled hydrocarbons via line 608 can be combined with the olefinic mixture via line 609 and compressed using one or more compressors 310. The compressed olefinic mixture via line 612 can exit the one or more compressors 310 at a pressure of from about 500 kPa to about 3000 kPa. In one or more embodiments, the pressure of the compressed olefinic mixture via line 612 can range from about 500 kPa (60 psig) to 3,000 kPa (420 psig); or from about 500 kPa (60 psig) to 1,000 kPa (130 psig). In one or more embodiments, the compressed olefinic mixture in line 612 can be at a temperature of from about 40° C. (100° F.) to about 300° C. (570° F.).

In one or more embodiments, the compressed olefinic mixture via line 612 can be treated using one or more treating units 315 to remove oxygenates, acid gases, water, or any combination thereof to provide a treated olefinic mixture via line 617. In one or more embodiments, the treated olefinic mixture via line 617 can include less than about 500 ppmv $H_2S$, less than about 50 ppmv $H_2S$, or less than about 1 ppmv $H_2S$. In one or more embodiments, the treated olefinic mixture in line 617 can include less than about 500 ppmv $CO_2$, less than about 100 ppmv $CO_2$, or less than about 50 ppmv $CO_2$.

In one or more embodiments, the treated olefinic mixture via line 617 can be dried in one or more drying units 320 to provide dried olefinic mixture via line 622. The dried olefinic mixture can include less than 100 ppmv water; less than 10 ppmv water; or less than 0.1 ppmv water. In one or more embodiments, the dried olefinic mixture can include less than 5 ppmv water; less than 1 ppmv water; or less than 0.5 ppmv water.

In one or more embodiments, the dried olefinic mixture in line 622 can be introduced to one or more de-propanizers 325 and selectively separated therein to provide an overhead containing $C_3$ and lighter hydrocarbons via line 627, and a bottoms containing $C_4$ and heavier hydrocarbons via line 629. In one or more embodiments, the $C_3$ and lighter hydrocarbons via line 627 can include 90% wt, 95% wt, or 99% Wt $C_3$ and lighter hydrocarbons. In one or more embodiments, the $C_3$ and lighter hydrocarbons can include hydrogen. The $C_3$ and lighter hydrocarbons can include from about 10% wt to about 40% wt $C_2$, from about 20% wt to about 70% wt $C_3$, and from about 0.1% wt to about 1% wt $H_2$. The $C_3$ and lighter hydrocarbons via line 627 can exit the de-propanizer 325 at a pressure of from about 500 kPa to about 2500 kPa. In one or more embodiments, the pressure of the $C_3$ and lighter hydrocarbons in line 627 can be from about 500 kPa (60 psig) to about 1,000 kPa (130 psig).

In one or more embodiments, the $C_4$ and heavier hydrocarbons via line 629 can include 90% wt, 95% wt, or 99% wt $C_4$-$C_{10}$ hydrocarbons. In one or more embodiments, the $C_4$ and heavier hydrocarbons via line 629 can include from about 30% wt to about 80% wt $C_4$, from about 5% wt to about 30% wt $C_5$, from about 5% wt to about 20% wt $C_6$, and from about 5% wt to about 20% wt $C_7$ and heavier hydrocarbons.

In one or more embodiments, the $C_4$ and heavier hydrocarbons via line 629 can be introduced to the one or more gasoline splitters 365 and selectively separated therein to provide an overhead containing $C_4$-$C_6$ hydrocarbons via line 667, and bottoms containing $C_7$ and heavier hydrocarbons via line 669. In one or more embodiments, the $C_7$ and heavier hydrocarbons can include about 80% wt, 90% wt, or 95% wt $C_4$-$C_6$, and from about 5% wt to about 80% wt $C_7$ and heavier hydrocarbons. In one or more embodiments, the $C_7$ and heavier hydrocarbons can include from about 40% wt to about 80% wt $C_4$, from about 5% wt to about 60% wt $C_5$, from about 1% wt to about 30% wt $C_6$, from about 1% wt to about 20% wt $C_7$, and from about 1% to about 10% wt $C_8$ and heavier hydrocarbons.

In one or more embodiments, at least a portion of the $C_4$-$C_6$ hydrocarbons via line 667 can be recycled directly to the cracker 100. For example, about 55% wt to about 65% wt; about 65% wt to about 75% wt; about 75% wt to about 85% wt; or about 85% wt to about 95% wt of $C_4$-$C_6$ hydrocarbons via line 667 can be recycled to the cracker 100. In one or more embodiments, about 10% wt to about 20% wt; about 20% wt to about 30% wt; about 30% wt to about 40% wt; or about 40% wt to about 50% wt of the $C_4$-$C_6$ hydrocarbons via line 667 can be recycled to the cracker 100. In one or more embodiments, at least a portion of the $C_4$-$C_6$ hydrocarbons via line 667 can be combined with the feedstock via line 115. In one or more embodiments, about 10% wt to about 20% wt; about 20% wt to about 30% wt; about 30% wt to about 40% wt; or about 40% wt to about 50% wt of $C_4$-$C_6$ hydrocarbons via line 667 can be combined with the feedstock via line 115. In one or more embodiments, about 5% wt to about 35% wt; about 15% wt to about 55% wt; about 45% wt to about 70% wt; about 60% wt to about 85% wt; or about 75% wt to about 100% wt of the $C_4$-$C_6$ hydrocarbons via line 667 can be combined with feedstock via line 115.

In one or more embodiments, the $C_4$-$C_6$ hydrocarbons via line 667 can include butanes and isobutanes. The $C_4$-$C_6$ hydrocarbons can include from about 10% wt to about 50% wt butanes. In one or more embodiments, the $C_4$-$C_6$ hydrocarbons can include from about 10% wt to about 50% wt isobutanes. The $C_4$-$C_6$ hydrocarbons via line 667 can include $C_4$-$C_6$ olefins from about 50% wt to about 90% wt $C_4$-$C_6$ olefins. In one or more embodiments, the $C_4$-$C_6$ hydrocarbons via line 667 can include from about 10% wt to about 50% wt $C_4$ olefins, from about 10% wt to about 50% wt $C_5$ olefins, and from about 5% wt to about 30% wt $C_6$ olefins.

In one or more embodiments, the $C_7$ and heavier hydrocarbons via line 669 can be stabilized using the one or more gasoline hydrotreaters 370 to provide a treated gasoline via line 672. In one or more embodiments, the treated gasoline can include from about 70% wt, 80% wt, or 90% wt $C_6$ and heavier hydrocarbons. In one or more embodiments, the treated gasoline can include from about 75% wt to about 85% wt $C_6$, from about 15% wt to about 25% wt $C_7$, and from about 5% wt to about 10% wt $C_8$ and heavier hydrocarbons.

In one or more embodiments, the treated gasoline in line 672 can be selectively separated using the one or more benzene/toluene/xylene ("BTX") units 375 to separate the aromatics via line 679, and a raffinate via line 677. In one or more embodiments, the aromatics concentration in line 679 can include about 40% wt, about 50% wt, about 60% wt, about 70% wt, or about 80% wt BTX. The aromatics can include from about 10% wt to about 40% wt benzene, from about 20% wt to about 60% wt toluene, and from about 10% wt to about 40% wt xylene. In one or more embodiments, at least a portion of the aromatics via line 679 can be directly recycled to the one or more crackers 100 (not shown in FIG. 6), or recycled to the one or more crackers 100 via line 115. In one or more embodiments, about 10% wt, about 20% wt, about 30% wt, or about 40% wt of the aromatics can be recycled to the cracker 100. In at least one specific embodiment, about 10% wt, about 15% wt, or about 20% wt of the aromatics can be recycled to the cracker 100.

In one or more embodiments, the raffinate via line 677 can be lean in aromatics. For example, the raffinate can include less than about 40% wt, 30% wt, 20% wt, or 10% wt BTX. In one or more embodiments, at least a portion of the raffinate in line 677 can be directly recycled to the steam pyrolytic cracker 602 (not shown in FIG. 6), or recycled to the steam pyrolytic cracker 602 via the alkane feed in line 601. In one or more embodiments, about 20% wt, about 30% wt, about 40% wt, or about 50% wt of the raffinate can be recycled to the steam pyrolytic cracker 602. In one or more embodiments, about 70% wt, about 80% wt, or about 90% wt of the raffinate in line 677 can be recycled to the steam pyrolytic cracker 602 via the alkane feed in line 601.

Returning to the de-propanizer 325, in one or more embodiments, the $C_3$ and lighter hydrocarbons exiting via line 627 can be compressed using the one or more compressors 330. In one or more embodiments, compressing the $C_3$ and lighter hydrocarbons can facilitate the separation of lighter hydrocarbons from the heavier hydrocarbons via line 627. The compressed $C_3$ and lighter hydrocarbons exiting the one or more compressors 330 via line 632 can have a pressure of about 500 kPa (60 psig) to about 3,500 kPa (490 psig). In one or more embodiments, the compressed $C_3$ and lighter hydrocarbons can exit the one or more compressors 330 at a pressure of about 500 kPa (60 psig) to about 1,500 kPa (200 psig). The compressed $C_3$ and lighter hydrocarbons can exit the one or more compressors 330 at a temperature of about 5° C. (40° F.) to about 100° C. (210° F.).

In one or more embodiments, the compressed $C_3$ and lighter hydrocarbons via line 632 can be chilled using the one or more chill trains 335 to provide chilled $C_3$ and lighter hydrocarbons via line 637. The chilled $C_3$ and lighter hydrocarbons can exit the one or more chill trains 335 at a temperature of about −40° C. (−40° F.) to about 40° C. (100° F.). In one or more embodiments, the chilled $C_3$ and lighter hydrocarbons can have a temperature from about −20° C. (−5° F.) to about 5° C. (40° F.).

In one or more embodiments, the chilled $C_3$ and lighter hydrocarbons can be introduced to the one or more de-methanizers 340 and selectively separated therein to provide an overhead containing methane via line 642 and a bottoms containing $C_2$ and $C_3$ hydrocarbons via line 644. In one or more embodiments, the de-methanizer overhead in line 642 can include from about 50% wt to about 95% wt methane. In one or more embodiments, the overhead in line 642 can include about 70% wt, about 80% wt, or about 90% wt methane. In one or more embodiments, the pressure of the overhead in line 642 can range from about 300 kPa (30 psig) to about 1,000 kPa (130 psig). In one or more embodiments, the de-methanizer bottoms in line 644 can include from about 20% wt to about 50% wt $C_2$ and from about 40% wt to about 80% wt $C_3$.

In one or more embodiments, the methane via line 642 can be directly recycled to the cracker 100 via line 115 (not shown in FIG. 6). In one or more embodiments, the methane exiting the de-methanizer 340 can be compressed using the one or more compressors 345 to provide a compressed methane via line 647 which can be recycled to the one or more crackers 100 via line 115, as shown. In one or more embodiments, about 15% vol to about 35% vol; about 20% vol to about 35% vol; about 25% vol to about 35% vol; or about 30% vol to 35% vol of the methane via line 642 can be recycled to the cracker 100. The compressed methane via line 647 can be at a pressure of about 100 kPa to about 1000 kPa, and a temperature of about 25° C. to about 200° C. In one or more embodiments, at least a portion of the methane in line 642 can be removed via line 642 as a final product.

In one or more embodiments, the $C_2$ and $C_3$ hydrocarbons via line 644 can be introduced to the one or more de-ethanizers 350 and selectively separated therein to provide an overhead containing a $C_2$ hydrocarbon mixture via line 652 and a bottoms containing a $C_3$ hydrocarbon mixture via line 654. In one or more embodiments, the overhead in line 652 can include about 90% wt, about 95% wt, or about 99% wt $C_2$. In one or more embodiments, the overhead in line 652 can include from about 5% wt to about 70% wt ethane and from about 30% wt to about 95% wt ethylene. In one or more embodiments, the bottoms in line 654 can include about 90% wt, about 95% wt, or about 99% wt $C_3$. In one or more embodiments, the bottoms in line 654 can include from about 5% wt to about 30% wt propane and from about 70% wt to about 95% wt propylene.

In one or more embodiments, the $C_2$ hydrocarbon mixture via line 652 can be introduced to the one more C2 splitters 355 and selectively separated therein to provide an overhead ("ethylene product") via line 357 and a bottoms ("ethane product") via line 359. In one or more embodiments, ethylene product in line 357 can include about 90% wt, about 95% wt, or about 99% wt ethylene. In one or more embodiments, the ethylene product in line 357 can include about 95% wt, about 99% wt, or about 99.9% wt ethylene. The ethane product in line 359 can include about 90% wt, about 95% wt, or about 99% wt ethane. In one or more embodiments, the ethane product in line 359 can include about 95% wt, about 99% wt, or about 99.9% wt ethane.

In one or more embodiments, the $C_3$ hydrocarbon mixture via line 654 can be introduced to one or more C3 splitters 360 and selectively separated therein to provide an overhead ("propylene product" or "second product") via line 362 and a bottoms ("propane product") via line 364. In one or more embodiments, the propane product in line 364 can include about 90% wt, about 95% wt, or about 99% wt propane. The propylene product in line 362 can include about 80% wt, about 90% wt, or about 95% wt propylene.

In one or more embodiments, all or any portion of the propylene product via line 362 can be recycled via line 663 to the hydrocarbon feed in line 115 and/or crackers 100 (not shown). Recycling at least a portion of the propylene to the cracker 100 via the hydrocarbon feed in line 115 can suppress propylene production in the one or more crackers 100, thereby preferentially increasing the ethylene yield. In one or more embodiments, about 10% vol to about 60% vol; about 20% vol to about 60% vol; about 30% vol to about 60% vol; about 40% vol to about 60% vol; or about 50% vol to about 60% vol of the propylene product in line 362 can be recycled via line 663 to the hydrocarbon feed in line 115 and/or crackers 100 (not shown). In one or more embodiments, about 60% vol to about 100% vol; about 70% vol to about 100% vol; about 80% vol to about 100% vol; or about 90% vol to about 100% vol of the propylene product in line 362 can be recycled via line 663 to the hydrocarbon feed in line 115 and/or crackers 100 (not shown).

In one or more embodiments, all or any portion of the ethane product via line 359 can be recycled to the one or more steam pyrolytic crackers 602 via the alkane feed in line 601. In one or more embodiments, all or any portion of the propane product via line 364 can be recycled to the one or more steam pyrolytic crackers 602 via the alkane feed in line 601. For example, about 60% vol to about 100% vol; about 70% vol to about 100% vol; about 80% vol to about 100% vol; or about 90% vol to about 100% vol of the ethane product via line 359 and about 70% vol to about 100% vol; about 80% vol to about 100% vol; or about 90% vol to about 100% vol of the propane product via line 364 can be recycled to the one or more steam pyrolytic crackers 602, either directly or via the alkane feed in line 601. In one or more embodiments, about 15% vol to about 55% vol; about 25% vol to about 55% vol; about 35% vol to about 55% vol; or about 45% vol to about 55% vol of the propane product via line 364 can be recycled to the one or more steam pyrolytic crackers 602. In one or more embodiments, about 15% vol to about 45% vol; about 25% vol to about 45% vol; or about 35% vol to about 45% vol of the ethane product via line 359 can be recycled to the one or more steam pyrolytic crackers 602. In one or more embodiments, at least a portion of the ethane product in line 359 can be removed as a finished product.

EXAMPLE

The foregoing discussion can be further described with reference to the following non-limiting examples. In the examples below, a gallium-containing doping agent, specifically dry gallium nitrate, was added to an FCC regeneration zone. Heptene was used for the hydrocarbon feed. The cracking operation, using the gallium doped catalyst, was in operation for approximately two (2) days. Catalyst inventory was 4,000 g and the catalyst rate was 20,000 g/hr. The hydrocarbon feed rate was maintained at about 1,000 g/hr. The hydrocarbon partial pressure was about 25 pounds per square inch absolute ("psia"). The gallium dosage rate was maintained at an equivalent of 30 g as gallium nitrate or 0.2% as gallium on a ZSM-5 catalyst. The results of the gallium additive to the regenerator compared to an identical process without the gallium addition are summarized in Table 1 below.

TABLE 1

Results of Gallium Additive to the Regenerator

|  | Without dopant | With dopant |
| --- | --- | --- |
| Liquid Yield (g/hr) | 307 | 375 |
| Liquid P/I/O/N/A | 14/5/35/4/40 | 12/4/32/3/48 |
| Ethylene Yield (wt %) | 11.9 | 13.5 |
| Propylene Yield (wt %) | 32.7 | 31.5 |
| Aromatic Yield (wt %) | 12.3 | 18.0 |

The term "P/I/O/N/A," as used in Table 1, refers to the relative percentage (by weight) of the following components: paraffins (P), isoparaffins (I), olefins (O), naphthalenes (N), and aromatics (A).

As shown in Table 1, the ethylene yield increased by about 10%, a significant amount in a price competitive market, and the propylene yield was about the same. Surprisingly, however, the aromatic yield increased by about 46%.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for producing one or more olefins, comprising:
doping a hydrocarbon cracking catalyst, comprising:
fluidizing one or more coked-catalyst particles in the presence of one or more oxidants to provide a fluidized mixture;
removing at least a portion of the coke from the one or more coked-catalyst particles to provide regenerated catalyst particles within the fluidized mixture;
distributing one or more doping agents to the fluidized mixture;
depositing the one or more doping agents onto a surface of the regenerated catalyst particles to provide doped catalyst particles;
forming a reaction mixture comprising one or more hydrocarbon feeds and the doped catalyst particles;
cracking at least a portion of the reaction mixture to provide a first product comprising propylene, ethylene, and butane;
selectively separating at least a portion of the first product to provide a second product comprising propylene and a first recycle comprising butane; and
recycling at least a portion of the first recycle to the one or more hydrocarbon feeds.

2. The process of claim 1, wherein the one or more doping agents comprises magnesium, barium, gallium, ruthenium, rhodium, palladium, or mixtures thereof.

3. The process of claim 1, further comprising increasing a temperature of the fluidized mixture above 480° C. prior to distributing the one or more doping agents.

4. The process of claim 1, wherein the hydrocarbon cracking catalyst comprises one or more zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), high activity zeolite catalysts, or any combination thereof.

5. The process of claim 1, wherein the one or more hydrocarbon feeds comprises methane, ethane, propane, butane, and pentane.

6. The process of claim 1, wherein the first product further comprises aromatic hydrocarbons, and wherein the first product comprises at least 10 wt % ethylene and at least 15 wt % aromatic hydrocarbons based on a weight of the one or more hydrocarbon feeds.

7. The process of claim 1, wherein the first product further comprises aromatic hydrocarbons, and wherein the first product comprises at least 10 wt % ethylene, at least 25 wt % propylene, and at least 15 wt % aromatic hydrocarbons based on a weight of the one or more hydrocarbon feeds.

8. The process of claim 1, wherein the doped catalyst particles produce about 10% or more ethylene in the first product relative to the regenerated catalyst particles without the one or more doping agents deposited thereon.

9. The process of claim 1, wherein the one or more doping agents increase an amount of ethylene and an amount of aromatic hydrocarbons and decrease an amount of propylene in the first product relative to the regenerated catalyst particles without the one or more doping agents deposited thereon.

10. The process of claim 1, wherein the doped catalyst particles contain about 0.2 wt % of the one or more doping agents based on a weight of the doped catalyst particles.

11. The process of claim 1, wherein the one or more doping agents is distributed to the fluidized mixture in the form of a mixture comprising the one or more doping agents and a supplemental fuel.

12. A process for producing one or more olefins, comprising:
doping a hydrocarbon cracking catalyst, comprising:
fluidizing one or more coked-catalyst particles in the presence of one or more oxidants to provide a fluidized mixture;
removing at least a portion of the coke from the one or more coked-catalyst particles to provide regenerated catalyst particles within the fluidized mixture;
distributing one or more doping agents to the fluidized mixture;
depositing the one or more doping agents onto a surface of the regenerated catalyst particles to provide doped catalyst particles;

forming a reaction mixture comprising one or more hydrocarbon feeds and the doped catalyst particles;

cracking at least a portion of the reaction mixture in a first reaction zone to provide a first product comprising propylene, ethylene, and butane;

cracking a refinery hydrocarbon comprising gas oil, full range gas oil, resid, or a combination thereof in a second reaction zone to provide a cracked hydrocarbon comprising ethylene, propylene, or a combination thereof;

combining the first product and the cracked hydrocarbon to form a first mixture;

selectively separating at least a portion of the first mixture to provide a second product comprising propylene and a first recycle comprising butane; and recycling at least a portion of the first recycle to the one or more hydrocarbon feeds.

13. The process of claim 12, wherein the first reaction zone is a first riser operating at a first temperature and a first pressure on a fluidized catalytic cracker; wherein the second reaction zone is a second riser operating at a second temperature and second pressure on the fluidized catalytic cracker; and wherein the first product and cracked hydrocarbon are combined within the fluidized catalytic cracker.

14. The process of claim 12, wherein the first reaction zone is a first riser operating at a first temperature and first pressure on a first fluidized catalytic cracker; wherein the second reaction zone is a first riser operating at a second temperature and second pressure on a second fluidized catalytic cracker; and wherein the first product and cracked hydrocarbon are combined outside of the first fluidized catalytic cracker and the second fluidized catalytic cracker.

15. The process of claim 12, wherein the one or more doping agents comprises magnesium, barium, gallium, ruthenium, rhodium, palladium, or mixtures thereof.

16. The process of claim 12, further comprising increasing a temperature of the fluidized mixture above 480° C. prior to distributing the one or more doping agents.

17. The process of claim 12, wherein the hydrocarbon cracking catalyst comprises one or more zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), high activity zeolite catalysts, or any combination thereof.

18. The process of claim 12, wherein at least one of the one or more hydrocarbon feeds comprises methane, ethane, propane, butane, and pentane.

19. A process for producing one or more olefins, comprising:

doping a hydrocarbon cracking catalyst, comprising:

fluidizing one or more coked-catalyst particles in the presence of one or more oxidants to provide a fluidized mixture;

removing at least a portion of the coke from the one or more coked-catalyst particles to provide regenerated catalyst particles within the fluidized mixture;

distributing one or more doping agents to the fluidized mixture;

depositing the one or more doping agents onto a surface of the regenerated catalyst particles to provide doped catalyst particles;

forming a reaction mixture comprising one or more hydrocarbon feeds and the doped catalyst particles;

cracking at least a portion of the reaction mixture in a first cracker to provide a first product comprising propylene, ethylene, and butane;

cracking a refinery hydrocarbon comprising gas oil, full range gas oil, resid, or a combination thereof in a second cracker to provide a cracked hydrocarbon comprising ethylene, propylene, or a combination thereof;

cracking one or more alkanes in a third cracker to provide an effluent comprising ethylene and propylene;

combining the first product and the cracked hydrocarbon to form a first mixture;

selectively separating at least a portion of the first mixture to provide a second product comprising propylene and a first recycle comprising butane; and recycling at least a portion of the first recycle to the one or more hydrocarbon feeds.

20. The process of claim 19, further comprising
recycling at least a portion of the first recycle to the first product.

21. The process of claim 19, further comprising combining the effluent with the first mixture prior to selectively separating the first mixture.

22. The process of claim 19, wherein the one or more doping agents comprises magnesium, barium, gallium, ruthenium, rhodium, palladium, or mixtures thereof.

23. The process of claim 19, further comprising increasing a temperature of the fluidized mixture above 480° C. prior to distributing the one or more doping agents.

24. The process of claim 19, wherein the hydrocarbon cracking catalyst comprises one or more zeolites, faujasite zeolites, modified faujasite zeolites, Y-type zeolites, ultrastable Y-type zeolites (USY), rare earth exchanged Y-type zeolites (REY), rare earth exchanged ultrastable Y-type zeolites (REUSY), rare earth free Z-21, Socony Mobil #5 zeolite (ZSM-5), high activity zeolite catalysts, or any combination thereof.

25. The process of claim 19, wherein at least one of the one or more hydrocarbon feeds comprises methane, ethane, propane, butane, and pentane.

26. The process of claim 19, wherein selectively separating at least a portion of the first mixture further provides a second recycle comprising methane; and the process further comprises recycling at least a portion of the second recycle to the one or more hydrocarbon feeds.

27. The process of claim 19, wherein selectively separating at least a portion of the first mixture further provides a second recycle comprising about 70 wt % or more methane; and the process further comprises recycling about 15 vol % to about 35 vol % of the second recycle to the one or more hydrocarbon feeds.

28. The process of claim 19, further comprising recycling about 10 vol % or more of the first product to the one or more hydrocarbon feeds.

* * * * *